(12) United States Patent
Aoki et al.

(10) Patent No.: US 8,386,193 B2
(45) Date of Patent: Feb. 26, 2013

(54) MOLECULAR ORBITAL COMPUTING DEVICE FOR ELONGATION METHOD

(75) Inventors: Yuriko Aoki, Fukuoka (JP); Feng Long Gu, Kasuga (JP); Jacek Korchowiec, Cracow (PL); Akira Imamura, Hiroshima (JP)

(73) Assignee: Japan Science and Technology Agency, Saitama (JP)

( * ) Notice: Subject to any disclaimer, the term of this patent is extended or adjusted under 35 U.S.C. 154(b) by 1736 days.

(21) Appl. No.: 11/663,945

(22) PCT Filed: Sep. 12, 2005

(86) PCT No.: PCT/JP2005/016767
§ 371 (c)(1),
(2), (4) Date: Mar. 27, 2007

(87) PCT Pub. No.: WO2006/035595
PCT Pub. Date: Apr. 6, 2006

(65) Prior Publication Data
US 2008/0059549 A1   Mar. 6, 2008

(30) Foreign Application Priority Data

Sep. 27, 2004 (JP) ............................ 2004-279278
Sep. 27, 2004 (JP) ............................ 2004-279315

(51) Int. Cl.
*G06F 17/10* (2006.01)
(52) U.S. Cl. .......................................... 702/27; 703/12
(58) Field of Classification Search .................. None
See application file for complete search history.

(56) References Cited

U.S. PATENT DOCUMENTS (Continued)

FOREIGN PATENT DOCUMENTS

| JP | 2000-298658 | 10/2000 |
|----|-------------|---------|
| JP | 2000-305923 | 11/2000 |

(Continued)

OTHER PUBLICATIONS

Korchowiec, J., Gu, F.L., Imamura, A., Kirtman, B. & Aoki, Y. Elongation method with cutoff technique for linear SCF scaling. International Journal of Quantum Chemistry 102, 785-794 (2005).*

(Continued)

*Primary Examiner* — Marjorie Moran
*Assistant Examiner* — Soren Harward
(74) *Attorney, Agent, or Firm* — Osha Liang LLP

(57) ABSTRACT

A molecular orbital computing device, method, program, and a recording medium recorded with the program, capable of computing electronic states at a high speed by an elongation method, are provided. A molecular orbital computing device (1) for determining molecular electronic states by the elongation method implements a localization process of transforming a canonical molecular orbital by an atomic orbital basis into a regional localized molecular orbital by using the formulas expressed by:

$$Y_{CMO}^{RLMO} = C_{RO}^{CML+} U$$

$$C_{AO}^{RLMO} = C_{AO}^{CMO} Y_{CMO}^{RLMO}$$

where $Y_{CMO}^{RLMO}$ is a transformation matrix for transforming into a regional localized molecular orbital by a canonical molecular orbital basis, $C_{RO}^{CMO+}$ is a transpose matrix of a matrix representing a canonical molecular orbital by a regional atomic orbital basis, U is a transformation matrix for erasing elements in an off-diagonal block in a density matrix $D^{RO}$ by the regional atomic orbital basis by a Jacobi method, $C_{AO}^{RLMO}$ is a matrix representing a regional localized molecular orbital by the atomic orbital basis, and $C_{AO}^{CMO}$ is a matrix representing the canonical molecular orbital by the atomic orbital basis.

3 Claims, 11 Drawing Sheets

U.S. PATENT DOCUMENTS

| | | |
|---|---|---|
| 6,799,151 B1 | 9/2004 | Yamada et al. |
| 2003/0204576 A1 | 10/2003 | Yamada et al. |
| 2006/0271301 A1 | 11/2006 | Takada et al. |

FOREIGN PATENT DOCUMENTS

| | | |
|---|---|---|
| JP | 2001-312485 | 11/2001 |
| JP | 2003-12567 | 1/2003 |
| JP | WO2005/029352 | 3/2005 |

OTHER PUBLICATIONS

Jensen, F. Introduction to Computational Chemistry. John Wiley & Sons (New York, NY). 1999. 1 page excerpt with 2 pages of front matter.*

Notice of Reasons for Rejection for Japanese Patent Application No. 2004-279278, Dated Dec. 22, 2009, and partial English translation thereof, 19 pages.

English Abstract from esp@cenet for Japanese patent application with Publication No. 2000-298568, Publication Date: Oct. 24, 2000, 1 page.

English Abstract from esp@cenet for Japan patent application with Publication No. 2000-305923, Publication Date: Nov. 2, 2000, 1 page.

English Abstract from esp@cenet for patent application with Publication No. 2001312485, Publication Date: Nov. 9, 2001, 1 page.

English Abstract from esp@cenet for Japanese patent application with Publication No. WO2005029352, Publication Date: Mar. 31, 2005, 1 page.

International Search Report for PCT/JP2005/016767 mailed Dec. 20, 2005 (1 page).

"A New Localization Scheme for the Elongation Method" Journal of Chemical Physics Dec. 1, 2004, vol. 121, No. 21, pp. 10385 to 10391.

"Cho Koritsuteki Kobunshi Bussei Kino Keisan System no Kaihatsu" Kagaku Kogyosha, Apr. 1, 2003, vol. 54, No. 4, pp. 1-18.

"Calculations of Phase Transition of Polydiacetylenes Using Localized Molecular Orbitals by Elongation Method" Journal of Chemical Physics Jun. 22, 1998, vol. 108, No. 24, pp. 10303 to 10308.

"A Theoretical Synthesis of Polymers by Using Uniform Localization of Molecular Orbitals: Proposal of an Elongation Method" Akira Imamura et al. J. Chem. Phys., 1991 vol. 95, pp. 5419-5431.

"Study Contents on Project" Akira Imamura et al. http://aoki.cube.kyushu-u.ac.jp/text/contents/JST_project/elongation_list.html Online—Retrieved Aug. 31, 2004.

esp@cenet Patent Abstract for JP2003012567 dated Jan. 15, 2003 (1 page).

Extended European Search Report for European Application No. 05778318.5-2201, mailed on Jan. 22, 2008 (12 pages).

Jong-Too Kim et al; "Theoretical Synthesis of Poly-(2-hydroxyethylmethacrylate) by Uniform Localization of Molecular Orbitals Calculation" Journal of Polymer Science, Part A (Polymer Chemistry) Wiley USA, vol. 39, No. 15, Aug. 1, 2001, pp. 2677-2682, XP002462861 (6 pages).

Mitani et al; "Geometry Optimization of Polymers by the Elongation Method" International Journal of Quantum Chemistry Wiley USA, vol. 64, No. 3, Aug. 25, 1997, pp. 301-323, XP002462862 (23 pages).

* cited by examiner

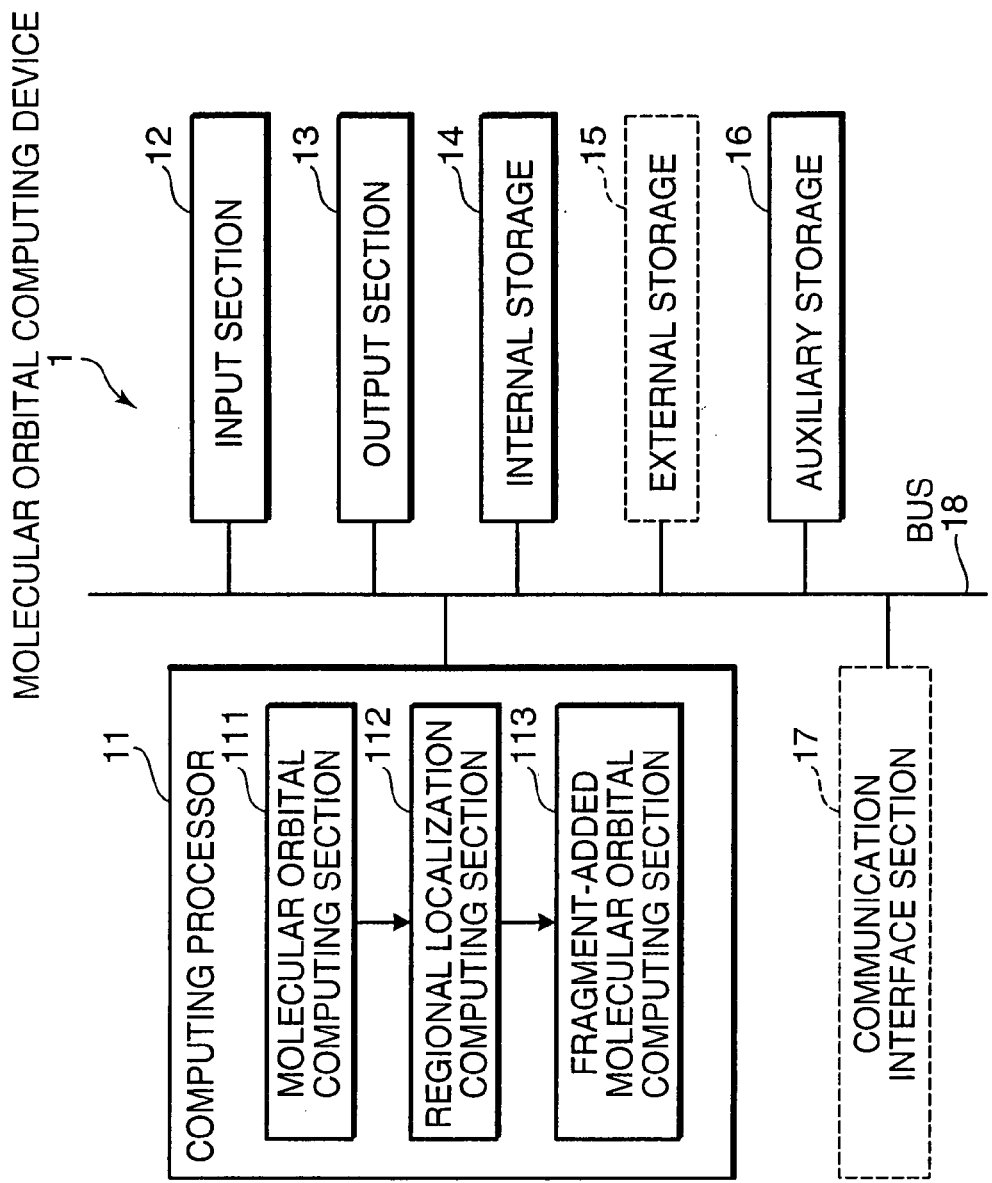

FIG.2A
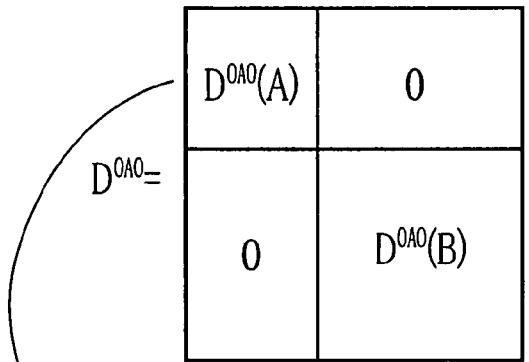
FIG.2B
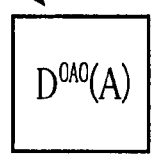
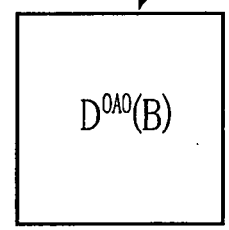
FIG.2C
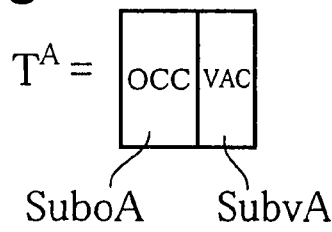
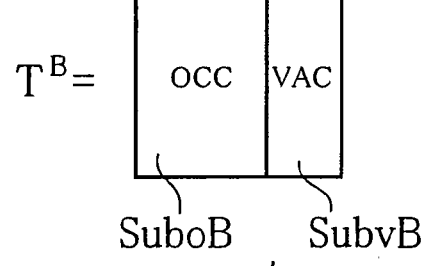
FIG.2D
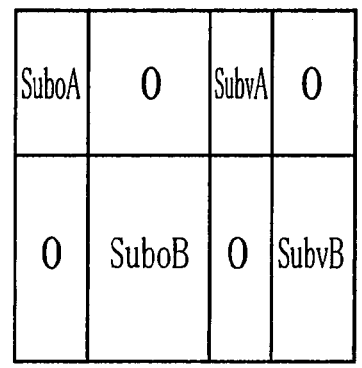

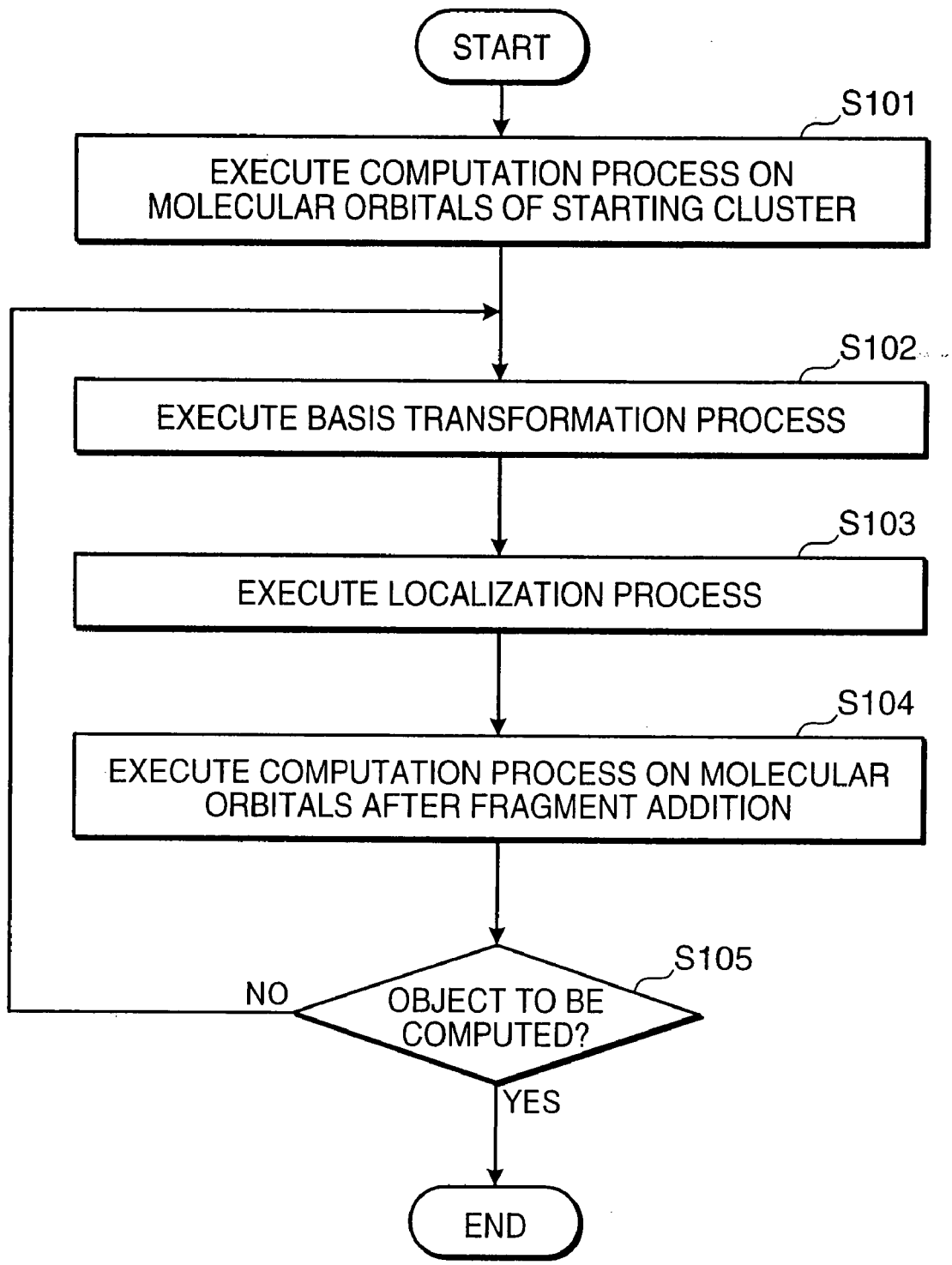

FIG.9A
CMO's
φi
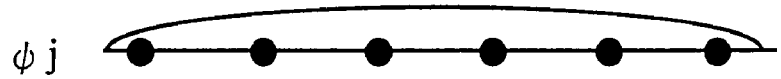
φj
↓ HYBRIDIZATION
FIG.9B
CMO's
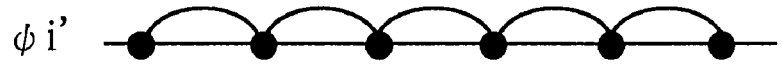
φi'
φj'
(HIBRIDIZED AO BASIS)
↓ UNIFORM LOCALIZATION
FIG.9C
LMO's
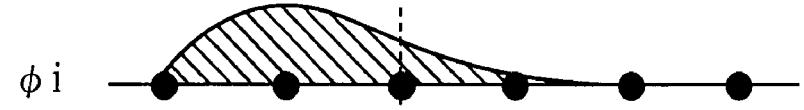
φi
A          B
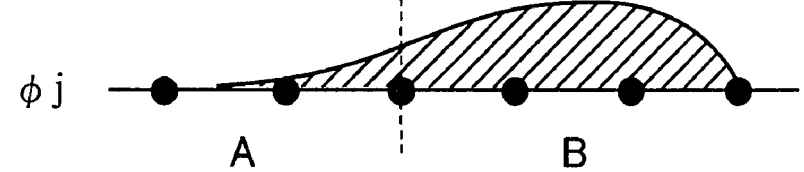
φj
A          B FROZEN LM Os ACTIVE LM Os

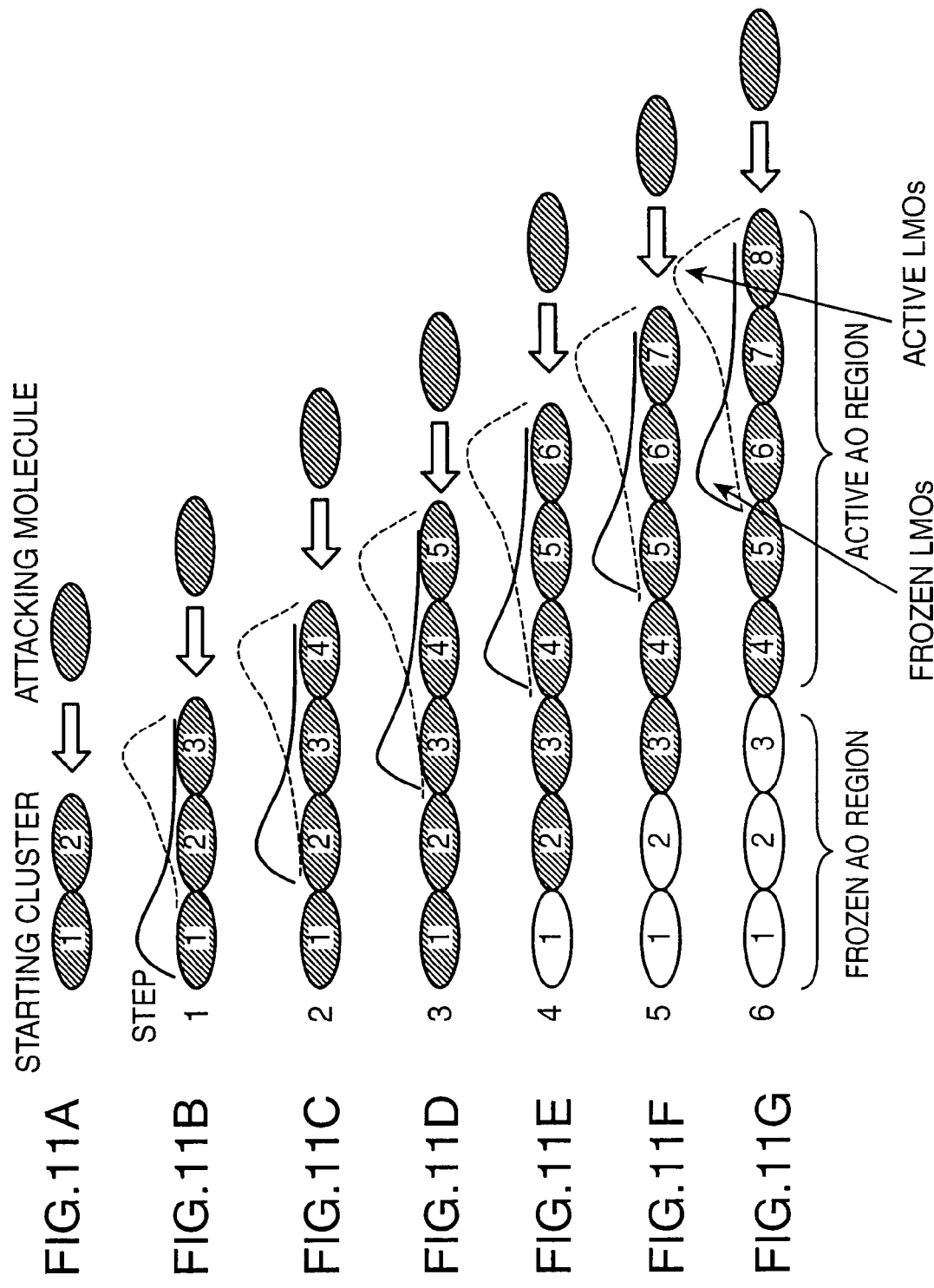

US 8,386,193 B2

MOLECULAR ORBITAL COMPUTING DEVICE FOR ELONGATION METHOD

TECHNICAL FIELD

The present invention relates to a molecular orbital computing device for determining molecular electronic states by an ab initio molecular orbital method, and more particularly to a molecular orbital computing device by an elongation method for determining molecular electronic states by applying a self consistent field method to the elongation method, a molecular orbital computing method by an elongation method, a molecular orbital computing program by an elongation method, and a recording medium recorded with the molecular orbital computing program by the elongation method.

BACKGROUND ART

Molecular characteristics are closely related to the kinds of atoms constituting molecules, or electronic states thereof. Elucidating molecular electronic states enables to perform an analysis on stable molecular structures which minimize molecular energies, transition state structures, normal vibrations, and the like by e.g. analytically obtaining derivations by an energy coordinate (so-called energy gradient method). Also, calculating potential energies with respect to a reaction coordinate in molecular reactions enables to obtain reaction systems, generation systems, reaction intermediates, and transition states, as equilibrium positions. Besides, various properties such as vibrational spectrum, electron spectrum, dipole moment, ionization potential, polarizability, and spin density can be obtained. Thus, elucidating molecular electronic states enables to know various molecular characteristics.

There is known a molecular orbital method, as a method for approximately determining molecular electronic states based on quantum mechanics. The molecular electronic states are represented by molecular orbitals. The molecular orbitals are obtained by solving an equation called Hartree-Fock-Roothaan equation (hereinafter, abbreviated as "HFR equation"). The HFR equation is an equation for determining set of spin orbitals which best approximates a system wave function to a basis state in the case where the system wave function is approximated by a single Slater determinant.

Also, the molecular orbital method is substantially classified, depending on the degree of approximation to be utilized in solving the HFR equation into: an empirically molecular orbital method, as represented by Hueckel method or extended Hueckel method; a semiempirically molecular orbital method, in which actual measurement values are used as computation parameters, while neglecting a specific term of a two-electron integral as a sufficiently small value; and an ab initio molecular orbital method for determining molecular electronic states by completely relying on computation based on the first principle without using actual measurement values except for the physical constants. Whereas the empirically molecular orbital method and the semiempirically molecular orbital method lack in reliability because the computation results depend on the approximation methods, parameters or the like, the ab initio molecular orbital method is superior in a point that the method is free from the drawback. There are known application programs of executing the ab initio molecular orbital method e.g. Gaussian 94/98/03 (product of Gaussian. Inc., U.S.A.) and GAMESS (product of NRCC, U.S.A.).

In the case where molecular electronic states are actually calculated by using the ab initio molecular orbital method, the calculation time is drastically increased, as the number N of atoms constituting a molecule is increased. Generally, the calculation time is conceived to be proportional to the third power or fourth power of the number N of atoms. Therefore, whereas it is possible to calculate the molecular electronic states within a reasonable time if the molecule consists of several atoms, it is impossible to calculate the molecular electronic states within a reasonable time if the molecule is a giant molecule consisting of multitudes of atoms such as polymers, which makes it substantially difficult to calculate the molecular electronic states.

In view of the above, some of the inventors of the invention have developed an elongation method for calculating electronic states of aperiodic polymers. The elongation method is a method for successively calculating electronic states of a targeted polymer by calculating the electronic states, with use of below-mentioned localized molecular orbitals (hereinafter, abbreviated as "LMOs"), each time a fragment is added, in place of using canonical molecular orbitals (hereinafter, abbreviated as "CMOs") basis, by successively adding monomers as additives (fragments) to an oligomer as a starting material (starting cluster) in such a manner as to trace a polymerization reaction of a polymer so that the starting cluster is elongated into the targeted polymer. The molecular orbital method for determining molecular electronic states by the elongation method is e.g. disclosed in the non-patent document 1, the non-patent document 2, the patent document 1, and the like, and will be summarized as follows.

FIG. 8 is a flowchart showing a molecular orbital computing method for determining molecular electronic states by the elongation method according to a background art. FIG. 9 is a diagram schematically showing molecular orbitals in respective steps to describe the molecular orbital computing method for determining molecular electronic states by the elongation method. FIG. 10 is a diagram for describing computations in adding fragments to active LMOs. FIG. 11 is a diagram for describing successive calculations in the elongation method.

Referring to FIGS. 8 through 11, the molecular orbital computing method for determining molecular electronic states by the elongation method includes a step of determining a starting cluster with respect to a targeted polymer whose electronic states are to be calculated, and obtaining CMOs by atomic orbitals (hereinafter, abbreviated as "AOs") basis of the starting cluster (S101). The initial starting cluster is a part of the targeted polymer consisting of a certain number of atoms, which includes one end of the targeted polymer, and has a length capable of constructing LMOs, and computing the electronic states by a known molecular orbital computing method. The expression "capable of constructing LMOs" means that an interaction by the atom at one end of the starting cluster does not substantially affect the atom at the other end thereof, and that an interaction by the atom at the other end does not substantially affect the atom at the one end. The length of the starting cluster may vary depending on the kinds of atoms constituting the starting cluster, but may normally be from 10 angstroms to 20 angstroms.

Next, the AOs basis for the molecular orbitals (hereinafter, abbreviated as "MOs") of the starting cluster is transformed into hybridized atomic orbitals (hereinafter, abbreviated as "HAOs") basis (Step S102). The CMOs by AOs basis obtained in Step S101 are distributed with respect to the entirety of the starting cluster, as schematically shown in FIG. 9(A). However, the transformation allows the CMOs by AOs basis to reside between the respective atoms of the starting cluster, as schematically shown in FIG. 9(B). The transformation can be computed by using the formulas 21 through 25.

$$S_{ax}S_{ax}^{\dagger}\overline{U}_{al} = \lambda_{ax}^{\ 1}\overline{U}_{al} \quad \text{(formula 21)}$$

where $S_{ax}$ is an overlap integral between atom "a" and atom "x" (x=b, c, d, e), and $S_{ax}^{+}$ is a transpose matrix of $S_{ax}$. In the following, similarly to the above, the superscript suffix "+" represents a transpose matrix. $\overline{U}_{al}$ (l=1, 2, 3, 4) is an eigenfunction of $S_{ax}S_{ax}^{+}$, $\lambda_{ax}^{\ 2}$ is an eigenvalue thereof, and b, c, d, e are respective orbitals of sp$^3$ hybridized orbital.

$$U_x = \overline{U}_x X_x \ (x=a, b, c, d, \ldots) \quad \text{(formula 22)}$$

where $U_x$ is a transformation matrix, and x=a, b, c, d, . . . .

$$\psi'_i = \sum_r \left( \sum_t C_{it} U_{rt} \right) \chi_r = \sum_r C'_{ir} \chi_r \quad \text{(formula 23)}$$

where C is a molecular orbital coefficient, with the original atomic orbital as a basis, and C' is a molecular orbital coefficient, with the hybridized orbital as a basis.

$$\psi'_j = \sum_s \left( \sum_u C_{ju} U_{su} \right) \chi_s = \sum_s C'_{js} \chi_s \quad \text{(formula 24)}$$

where, similarly to the above, $\psi'_j$ is the j-th molecular orbital by hybridized orbital basis, and $\chi_s$ is the atomic orbital.

$$F'C' = S'C'E \quad \text{(formula 25)}$$

where F' is expressed by the formula 25-1, S' is expressed by the formula 25-2, and C' is expressed by the formula 25-3.

$$F' = U^{\dagger} F U \quad \text{(formula 25-1)}$$

$$S' = U^{\dagger} S U \quad \text{(formula 25-2)}$$

$$C' = U^{\dagger} C \quad \text{(formula 25-3)}$$

Next, LMOs by AOs basis of the starting cluster which have been localized in such a manner that the phase of the orbital is increased at a specific site are created based on CMOs by HAOs basis of the starting cluster (S103). In creation of LMOs by AOs basis, as schematically shown in FIG. 9(C), there are created frozen LMOs $\phi_i$ which have been localized in such a manner that the phase of the orbital is increased on one end (frozen LMO region A or frozen LMO part) of the starting cluster to which a fragment is not added, and created active LMOs $\phi_j$ which have been localized in such a manner that the phase of the orbital is increased on the other end (active LMO region B or active LMO part) of the starting cluster to which a fragment is added. The starting cluster is sorted into the frozen LMO region and the active LMO region because it is conceived that an interaction between the starting cluster and the fragment occurs solely on the other end (reaction end) of the starting cluster to which the fragment is added, and that an interaction at the one end of the starting cluster to which the fragment is not added may be of a substantially negligible degree. The localization process of creating LMOs by AOs basis can be computed by using the formulas 26 through 31.

$$\phi_i = \sin\theta \psi'_i + \cos\theta \psi'_j \quad \text{(formula 26)}$$

$$\phi_j = -\cos\theta \psi'_i + \sin\theta \psi'_j \quad \text{(formula 27)}$$

$$\phi = \left( \sum_r^{on\ A} + \sum_r^{on\ B} \right)(\sin\theta C'_{ir} + \cos\theta C'_{jr})\chi_r \quad \text{(formula 28)}$$

$$= \phi_i(A) + \phi_i(B)$$

$$\phi_j = \left( \sum_s^{on\ A} + \sum_s^{on\ B} \right)(-\cos\theta C'_{is} + \sin\theta C'_{js})\chi_s \quad \text{(formula 29)}$$

$$= \phi_j(A) + \phi_j(B)$$

$$L_{ij} = \langle \phi_i(A) | \phi_i(A) \rangle + \langle \phi_j(B) | \phi_j(B) \rangle \quad \text{(formula 30)}$$

$$L_{ij} = \alpha_{ij}\sin^2\theta + 2\gamma_{ij}\sin\theta\cos\theta + \beta_{ij}\cos^2\theta \quad \text{(formula 31)}$$

where $\alpha_{ij}$ is expressed by the formula 31-1, $\beta_{ij}$ is expressed by the formula 31-2, $\gamma_{ij}$ is expressed by the formula 31-3, $\theta$ is expressed by the formula 31-4, and $\omega$ is expressed by formula 31-5.

$$\alpha_{ij} = \sum_r^{on\ A} \sum_s^{on\ A} C'_{ir} C'_{is} S'_{rs} + \sum_r^{on\ B} \sum_s^{on\ B} C'_{jr} C'_{js} S'_{rs} \quad \text{(formula 31-1)}$$

$$\beta_{ij} = \sum_r^{on\ A} \sum_s^{on\ A} C'_{jr} C'_{js} S'_{rs} + \sum_r^{on\ B} \sum_s^{on\ B} C'_{ir} C'_{is} S'_{rs} \quad \text{(formula 31-2)}$$

$$\gamma_{ij} = \sum_r^{on\ A} \sum_s^{on\ A} C'_{ir} C'_{js} S'_{rs} - \sum_r^{on\ B} \sum_s^{on\ B} C'_{ir} C'_{js} S'_{rs} \quad \text{(formula 31-3)}$$

$$\theta_{ext} = \left( \frac{\pi}{4} - \frac{\omega}{2} \right) \quad \text{(formula 31-4)}$$

$$\omega = \tan^{-1}\left\{ \frac{\beta_{ij} - \alpha_{ij}}{2\gamma_{ij}} \right\} \quad \text{(formula 31-5)}$$

Next, MO in the case where fragments are added to the starting cluster is computed (S104). The molecular electronic states can be determined by e.g. solving a Fock matrix (F matrix) by a self-consistent field (SCF) method. According to the SCF method, a new electron density is obtained by diagonalizing the F matrix, using an initial electron density. Then, another new electron density is obtained by diagonalizing the F matrix, by using the newly obtained electron density as an initial electron density. This operation is iteratively executed until the electron density defined as the initial electron density is substantially equal to the electron density obtained by diagonalizing the F matrix. The F matrix is solved by conducing the aforementioned procedure in the SCF method.

In the SCF method, normally, diagonalization of the AO-based Fock matrix $F_{AO}$ shown in FIG. 10C is required. With use of LMOs basis, however, as schematically shown in FIGS. 10A and 10B, a fragment (attacking molecule) is exclusively interacted with active LMOs. Accordingly, concerning the Fock matrix $F_{AO}$, the SCF method is executed solely with respect to the lower right regional parts of $F_{LMO22}$, $F_{LMO23}$, $F_{LMO32}$, and $F_{LMO33}$, because the respective elements in inverse L-shaped regional parts of $F_{LMO11}$, $F_{LMO12}$, $F_{LMO13}$, $F_{LMO21}$, and $F_{LMO31}$ shown in FIG. 10C can be regarded as zero. Thus, as compared with a molecular orbital computing method in which all the systems are processed, the above method is advantageous in reducing the calculation amount, and providing efficient and high-speed computation.

Here, $F_{LMO11}$ are interaction-related matrix elements in which the respective orbitals of frozen LMOs are acted with the orbitals thereof. $F_{LMO12}$ are interaction-related matrix elements in which the respective orbitals of frozen LMOs are acted with the orbitals of active LMOs. $F_{LMO13}$ are interaction-related matrix elements in which the respective orbitals of frozen LMOs are acted with the orbitals of fragments. $F_{LMO21}$ are interaction-related matrix elements in which the respective orbitals of active LMOs are acted with the orbitals of frozen LMOs. $F_{LMO22}$ are interaction-related matrix elements in which the respective orbitals of active LMOs are acted with the orbitals thereof. $F_{LMO23}$ are interaction-related matrix elements in which the respective orbitals of active LMOs are acted with the orbitals of fragments. $F_{LMO31}$ are interaction-related matrix elements in which the respective orbitals of fragments are acted with the orbitals of frozen LMOs. $F_{LMO32}$ are interaction-related matrix elements in which the respective orbitals of fragments are acted with the orbitals of active LMOs. $F_{LMO33}$ are interaction-related matrix elements in which the respective orbitals of fragments are acted with the orbitals thereof.

The fragment-added molecular orbital computation process of computing MO in the case where a fragment is added to the starting cluster is expressed by the formulas 32 and 33. Specifically, computation is implemented solely with respect to the lower right part of the formula 32 partitioned by the broken lines.

$$\begin{vmatrix} H^{occ}(A,A)-\varepsilon I & 0 & H^{occ}(A,B) & 0 & \sim 0 \\ 0 & H^{vac}(A,A)-\varepsilon I & 0 & H^{vac}(A,B) & \sim 0 \\ H^{occ}(B,A) & 0 & H^{occ}(B,B)-\varepsilon I & 0 & H^{occ}(B,M)-\varepsilon S^{occ}(B,M) \\ 0 & H^{vac}(A,A)-\varepsilon I & 0 & H^{vac}(B,B)-\varepsilon I & H^{vac}(B,M)-\varepsilon S^{vac}(B,M) \\ \sim 0 & \sim 0 & H^{occ}(M,B)-\varepsilon S^{occ}(M,B) & H^{vac}(M,B)-\varepsilon S^{vac}(M,B) & H(M)-\varepsilon I \end{vmatrix} = 0$$

(formula 32)

where $H_{ij}^{OCC}(X,Y)$ is expressed by the formula 33.

$$H_{ij}^{OCC}(X,Y) = \int \phi_j^{(OCC,X)} H \phi_j^{(OCC,Y)} d\tau \quad \text{(formula 33)}$$

where $\phi_j^{(OCC,X)}$ is the j-th occupied orbital which has been localized to the region X (X is a frozen region or an active region).

Next, judgment is made as to whether a resultant obtained by adding a fragment to the starting cluster is a targeted polymer (S105). If the judgment result indicates that the resultant is not the targeted polymer, the routine returns to Step S102 by regarding the resultant in Step S104 obtained by adding the fragment to the starting cluster, as a new starting cluster. If, on the other hand, the judgment result indicates that the resultant is the targeted polymer, the molecular orbital computation is ended.

By implementing the aforementioned operations, as shown in FIG. 11A to 11G, the electronic states are successively computed, each time a fragment is added, while successively adding the fragment to the starting cluster. Referring to FIG. 11, the oval-shaped marks represent fragments. For instance, if a targeted material whose electronic states are to be calculated is a polymer, the fragments are monomers.

Since interaction with a fragment is not acted on the end part (frozen AO region) remotely away from the active LMO region, the electronic states can be fixed at the end part. Accordingly, in the iterative calculations from Step S102 through Step S105, the end part can be eliminated from a targeted object to be calculated. Therefore, the iterative calculations from Step S102 through Step S105 are implemented with respect to a region (active AO region) having a certain length. Also, the active AO region is sequentially shifted to the other end of the resultant to which a fragment is added, each time the fragment is added. In this way, the molecular electronic states after the fragment addition can be computed efficiently without lowering calculation precision. The frozen AO region is a region where interaction with a fragment at the frozen LMO is equal to or smaller than a predetermined threshold value (e.g. $10^{-5}$ a.u. or $10^{-6}$ a.u., a.u. represents atom unit).

In the example schematically shown in FIGS. 11A to 11G, the starting cluster as shown in FIG. 11A consists of two fragments, and five fragments constitute an active AO region, as shown in FIG. 11D. Therefore, as shown in FIG. 1E, if the resultant is constituted of six fragments, a frozen AO region with one fragment is generated. Then, as shown in FIGS. 11F and 11G, each time a fragment is added, the frozen AO region is successively extended toward the other end of the resultant to which the fragment is added. Also, the active AO region is successively shifted toward the other end of the resultant to which the fragment is added.

Here, referring to FIGS. 11A to 11G, the oval-shaped marks shown by the hatched portions represent fragments of an active AO region, and the oval-shaped marks shown by the hollow portions represent fragments of a frozen AO region. Further, in the examples shown in FIGS. 11A to 11G, frozen LMOs and active LMOs are formed respectively in such a manner that the orbitals are localized with respect to two fragments at one end of the resultant to which a fragment is added, and the orbitals are localized with respect to one fragment at the other end of the resultant to which a fragment is added. The region where the frozen LMOs and the active LMOs are formed, in other words, a region (region corresponding to three fragment lengths in FIGS. 11A to 11G) consisting of a frozen LMO region A and an active LMO region B is called as a localized region.

The molecular orbital computing method for determining molecular electronic states by the elongation method according to the background art is a method based on a premise that fragments are sequentially added to a starting cluster with respect to a giant molecule whose electronic states are to be calculated. The method includes: creating LMOs on the starting cluster which have been localized to an active LMO region strongly interacted with the MOs of the fragment by a proper unitary transformation; and solving an eigenvalue problem by the SCF method in association with the CMOs on the fragment to determine the electronic states of the entirety of the giant molecule.

The aforementioned localization process requires a unitary transformation. The unitary transformation includes: arbitrarily selecting two CMOs in pairs from the CMOs; transforming the CMOs in pairs into MO which has been localized to a frozen LMO region and an active LMO region, respectively; and iteratively executing the transformation until convergence is seen with respect to all the pairs.

The convergence is particularly slow in a system where non-localization of orbitals is strong. Therefore, the calculation time is unduly increased in a large basis set.

Also, in the localization process, localization is executed after the CMOs are sorted into the MOs which have been localized to the frozen LMO region and the active LMO region, respectively. The transformation is conducted by selecting two orbitals in pairs individually, which requires an unduly long time for convergence of localization, and consequently may lower precision concerning computation results.

non patent document 1: "A theoretical synthesis of polymers by using uniform localization of molecularorbirals: Proposal of an elongation method" by Akira Imamura, Yuriko Aoki, and Koji Maekawa, J. Chem. Phys., Vol. 95, pp. 5419-5431 (1991)

non patent document 2: "Study contents on project", [online], internet <http://aoki.cube.Kyushu-u.ac.jp/text/contents/JST_project/JST_content_new.html> [retrieved on Aug. 31, 2004]

patent document 1: Japanese Unexamined Patent Publication No. 2003-012567

DISCLOSURE OF THE INVENTION

In view of the above, it is an object of the invention to provide a molecular orbital computing device by an elongation method, capable of performing a high-speed analysis, as compared with the background art, as well as a molecular orbital computing method by an elongation method, a molecular orbital computing program by an elongation method, and a recording medium recorded with the molecular orbital computing program by the elongation method.

According to the invention, in obtaining molecular electronic states by an elongation method, a localization process of transforming a canonical molecular orbital by an atomic orbital basis into a regional localized molecular orbital is implemented, by using the formulas expressed by the below-mentioned formulas 13 and 14, where $Y_{CMO}^{RLMO}$ is a transformation matrix for transforming into a regional localized molecular orbital by a canonical molecular orbital basis, $C_{RO}^{CMO+}$ is a transpose matrix of a matrix representing a canonical molecular orbital by a regional atomic orbital basis, U is a transformation matrix for erasing elements in an off-diagonal block in a density matrix $D^{RO}$ by the regional atomic orbital basis by a Jacobi method, $C_{AO}^{RLMO}$ is a matrix representing a regional localized molecular orbital by the atomic orbital basis, and $C_{AO}^{CMO}$ is a matrix representing the canonical molecular orbital by the atomic orbital basis.

As mentioned above, implemented is the localization process of directly transforming the canonical molecular orbital by the atomic orbital basis into the canonical molecular orbital by the regional localized molecular orbital basis, by using the formulas expressed by the below-mentioned formulas 13 and 14. Unlike the background art, this eliminates the need of a process of: arbitrarily selecting two CMOs in pairs from the CMOs; transforming the CMOs in pairs into MO which has been respectively localized to a frozen LMO region and an active LMO region; and iteratively executing the transformation until convergence is seen with respect to all the pairs. With this arrangement, a high-speed regional localization process can be executed, as compared with the localization process according to the background art. Also, this arrangement eliminates an arbitrary property, which may be generated in sorting the CMOs into MO which has been respectively localized to the frozen LMO region and the active LMO region.

BRIEF DESCRIPTION OF THE DRAWINGS

FIG. 1 is a block diagram showing a configuration of a molecular orbital computing device by an elongation method.

FIGS. 2A through 2D are diagrams for describing an approach for obtaining a transformation matrix T for transforming a density matrix $D^{OAO}$ by an orthogonal atomic orbital basis into a regional atomic orbital RO.

FIG. 8 is a flowchart showing a molecular orbital computing method for determining molecular electronic states by an elongation method according to the background art.

FIG. 9 is a diagram schematically showing molecular orbitals in the respective steps for describing the molecular orbital computing method for determining molecular electronic states by the elongation method according to the background art.

FIGS. 11A to 11G are diagrams for describing successive calculations by an elongation method.

BEST MODE FOR CARRYING OUT THE INVENTION

Figure 3:
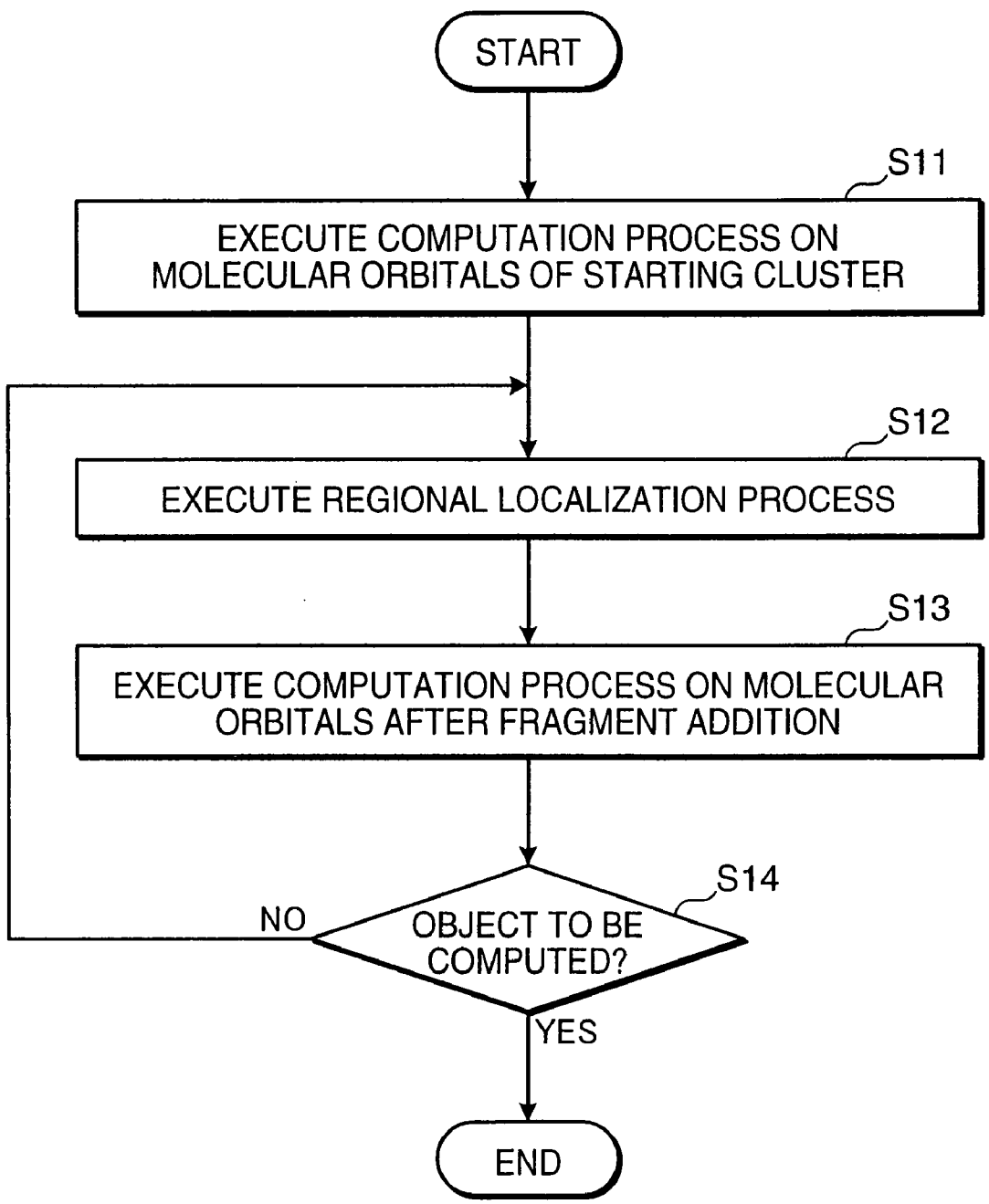
FIG. 3 is a flowchart showing an operation of the molecular orbital computing device by the elongation method.

In the following, an embodiment of the invention is described referring to the drawings. Elements with the same reference numerals throughout the drawings are identical or equivalent elements to each other, and accordingly, repetitive description thereof will be omitted herein.

Construction of Embodiment

FIG. 1 is a block diagram showing a configuration of a molecular orbital computing device by an elongation method. FIGS. 2A through 2D are diagrams for describing an approach for obtaining a transformation matrix T of transforming a density matrix $D^{OAO}$ by an orthogonal atomic orbital basis into a regional atomic orbital RO.

Referring to FIG. 1, the molecular orbital computing device 1 by the elongation method includes a computing processor 11, an input section 12, an output section 13, an internal storage 14, an auxiliary storage 16, and a bus 18.

The computing processor 11 has e.g. a microprocessor and its peripheral circuits. Functionally, the computing processor 11 includes a molecular orbital computing section 111, a regional localization computing section 112, and a fragment-added molecular orbital computing section 113. The computing processor 11 controls the input section 12, the output section 13, the internal storage 14, and the auxiliary storage 16 depending on the relevant functions of the functional elements in accordance with a control program.

The molecular orbital computing section 111 computes CMOs by AO basis of a starting cluster by a well-known molecular orbital computing method. The well-known molecular orbital computing method is e.g. disclosed in "Chemistry new series; molecular orbital method" by Minoru Hirota, published by Shokabo, first print published on Apr. 30, 1999.

The regional localization computing section 112 directly transforms CMOs by AO basis of a starting cluster into CMOs by LMO basis by using a below-mentioned transformation matrix Y.

The transformation matrix Y can be obtained by implementing the following procedure. First, a density matrix D by AO basis is expressed by the formula 1.

$$D^{AO} = C_{AO}^{CMO} d C_{AO}^{CMO\dagger} \qquad \text{(formula 1)}$$

where C is a canonical molecular orbital, the superscript suffix shows a new state of the canonical molecular orbital, and the subscript suffix shows a basis thereof. Concerning the below-mentioned description, the same definition as mentioned above is applied. Accordingly, $C_{AO}^{CMO}$ is a canonical molecular orbital by AO basis, and d is a diagonal occupation number matrix. Transformation from AO to CMO is defined by the formula 2. Since the number of alphabets is limited, it is not always the case that the same characters or symbols disclosed in the best mode for carrying out the invention as those used in the background art have the same meaning.

$$\varphi_i^{CMO} = \sum_m (C_{AO}^{CMO})_{mi} \chi_m^{AO} \qquad \text{(formula 2)}$$

where $\phi_i^{CMO}$ is the i-th canonical orbital, and $\chi_m^{AO}$ is the m-th atomic orbital.

Concerning a restricted Hartree-Fock wave function, the occupation number is either 2 or 0 depending on whether the orbital is a doubly occupied orbital or a non-occupied orbital. In the case where CMO satisfies the formula 3, which is an ortho-normalization condition, with an overlap integral $S^{AO}$ of AO, the formula 1 satisfies the formula 4.

$$C_{AO}^{CMO\dagger} S^{AO} C_{AO}^{CMO} = 1 \qquad \text{(formula 3)}$$

$$D^{AO} S^{AO} D^{AO} = 2 D^{AO} \qquad \text{(formula 4)}$$

Here, transforming a non-orthogonal atomic orbital basis into an orthogonal atomic orbital (OAO) basis enables to proceed the calculation smoothly. In view of this, Loewdin's symmetric orthogonalization which minimizes a deviation from the original basis set is employed. The original basis set is generally a canonical orbital obtained by a non-orthogonal atomic orbital basis. A transformation matrix X of transforming the density matrix $D^{AO}$ by non-orthogonal atomic orbital basis into an orthogonal atomic orbital basis is obtained by diagonalizing $S^{AO}$, and is expressed by the formula 5.

$$X = V e^{1/2} V^\dagger = X^\dagger \qquad \text{(formula 5)}$$

where V is an eigenvector of $S^{AO}$, and e is an eigenvalue of $S^{AO}$. Accordingly, the density matrix $D^{OAO}$ by orthogonal orbital basis is expressed by the formula 6.

$$D^{OAO} = X D^{AO} X^\dagger \qquad \text{(formula 6)}$$

Accordingly, the formula 7 is derived based on the formulas 1, 6, and the formula: $X^+X = XX^+ = S^{AO}$.

$$D^{OAO} D^{OAO} = 2 D^{OAO} \qquad \text{(formula 7)}$$

As is obvious from the formula 7, the eigenvalue of $D^{OAO}$ should be either one of 2 and 0. If the eigenvalue is 2, the orbital is a doubly occupied orbital, and if the eigenvalue is 0, the orbital is a non-occupied orbital.

Next, occupied orbitals and non-occupied orbitals with respect to the frozen region and the active region are obtained. These orbitals are called as "regional localized molecular orbitals" (hereinafter, abbreviated as "RLMOs").

Referring to FIGS. 2A through 2D, in order to obtain occupied orbitals and non-occupied orbitals with respect to the frozen LMO region and the active LMO region, first, as shown in FIGS. 2A and 2B, a sub block of $D^{OAO}$ is sorted into $D^{OAO}$ (A) in the frozen LMO region, and $D^{OAO}$ (B) in the active LMO region. By diagonalizing $D^{OAO}$ (A) and $D^{OAO}$ (B), a regional atomic orbital space is defined. In the diagonalization, the eigenvector T of $D^{OAO}$ (A) and the eigenvector $T^B$ of $D^{OAO}$ (B) are respectively sorted into doubly occupied orbitals, singly occupied orbitals, and empty (non-occupied) orbitals, concerning the regional atomic orbitals (hereinafter, abbreviated as "ROs"). Accordingly, $T^A$ and $T^B$ are, as shown in FIG. 2C, sorted into the left-side sub blocks SuboA and SuboB shown by "occ" in the drawing, in which the respective matrix elements are constituted of elements of doubly occupied orbitals and singly occupied orbitals; and the right-side sub blocks SubvA and SubvB shown by "vac" in the drawing, in which the respective matrix elements are constituted of elements of non-occupied orbitals. Specifically, assuming that $T^A$ is a matrix consisting of "a" rows and "b" columns, wherein the elements from the first to the m-th column are elements of doubly occupied orbitals and singly occupied orbitals, SuboA is a block from the first column to the m-th column, and SubvA is a block from the (m+1)-th column to the b-th column, where m<b, n<d. Also, assuming that $T^B$ is a matrix consisting of "c" rows and "d" columns, wherein the elements from the first to the n-th column are elements of doubly occupied orbitals and singly occupied orbitals, SuboB is a block from the first column to the n-th column, and SubvB is a block from the (n+1)-th column to the d-th column. Since the singly occupied orbitals in the frozen LMO region constitute pairs of bonding/anti-bonding, the singly occupied orbitals are hybridized bonding orbitals which are bonded to hybridized bonding orbitals of singly occupied orbitals in the active LMO region. In this condition, by fugitively transferring from the respective singly occupied orbitals in the frozen LMO region to the singly occupied orbitals in the active LMO region, all the ROs can be approximated to either one of doubly occupied orbitals and non-occupied orbitals. Also, concerning the non-bonding systems which are bonded to water molecules by hydrogen bonding, naturally, all the ROs are doubly occupied orbitals and non-occupied orbitals. Accordingly, the transformation matrix T of transforming the density matrix $D^{OAO}$ by orthogonal atomic orbital basis into regional orbitals RO is, as shown in FIG. 2D, is a matrix, wherein the elements from the first row and the first column to the a-th row and the m-th column are the elements of SuboA, the elements from the first row and the (m+1)-th column to the a-th row and the (m+n)-th column are 0, the elements from the first row and the (m+n+1)-th column to the a-th row and the (b+n)-th column are the elements of SuboA, the elements from the first row and the (b+n+1)-th column to the a-throw and the (b+d)-th column are 0, the elements from the (a+1)-th row and the first column to the (a+c)-th row and the m-th column are 0, the elements from the (a+1)-th row and the (m+1)-th column to the (a+c)-th row and the (m+n)-th column are the elements of SuboB, the elements from the (a+1)-th row and the (m+n+1)-th column to the (a+c)-th row and the (b+n)-th column are 0, and the elements from the (a+1)-th row and the (b+n+1)-th column to the (a+c)-th row and the (b+d)-th column are the elements of SuboB.

If an operator for obtaining T based on $T^A$ and $T^B$ by the aforementioned computation method is expressed as "$", T can be expressed by the formula 8.

$$T = T^A \$ T^B \quad \text{(formula 8)}$$

By implementing the formula 8, the density matrix D of RO is expressed by the formula 9, and a matrix of transforming from the canonical molecular orbital CMO to the regional atomic orbital RO is given by $T^+X$ in the formula 10.

$$D^{RO} = T^\dagger D^{OAO} T \quad \text{(formula 9)}$$

$$C_{RO}^{CMO} = T^\dagger X C_{AO}^{CMO} \quad \text{(formula 10)}$$

Accordingly, the formula 11 is derived from the formula 7 and the unitary condition: $TT^+ = T^+T = 1$.

$$D^{RO} D^{RO} = 2 D^{RO} \quad \text{(formula 11)}$$

RO given by the formula 11 is substantially localized to the frozen LMO region and the active LMO region except for a portion where the orbitals in the frozen LMO region are extended toward the active LMO region and a portion where the orbitals in the active LMO region are extended toward the frozen LMO region, but is not completely turned into any one of the occupied orbitals and the non-occupied orbitals. In view of this, a unitary transformation is conducted so that localization is substantially carried out between the occupied orbitals and the non-occupied orbitals concerning $D^{RO}$, so that the computation result is on the order of $10^{-6}$ or less or $10^{-7}$ or less, for instance. This is a Jacobi method similar to the one conducted in e.g. the below-mentioned document to transform a natural bond orbital (NBO) into a localized molecular orbital.

document: A. E. Reed and F. Weinhold, J. Chem. Phys. 83, pp. 1736 (1985)

Concerning the density matrix $D^{RO}$ by regional atomic orbital basis, if the formula 12 is satisfied, by using the transformation matrix U for erasing the elements in an off-diagonal block by a Jacobi method, the elements in the density matrix D by regional localized molecular orbital (RLMO) basis which are not 0 become 2. The transformation from AO basis to RLMO basis is given by the formula 14, because the transformation matrix Y is expressed by the formula 13. Although RLMO basis corresponds to LMO basis, RLMO basis is called as such to show that a derivation method for RLMO basis is different from the corresponding one in the background art.

$$D^{RLMO} = U^\dagger D^{RO} U \quad \text{(formula 12)}$$

$$Y_{CMO}^{RLMO} = C_{RO}^{CMO\dagger} U \quad \text{(formula 13)}$$

$$C_{AO}^{RLMO} = C_{AO}^{CMO} Y_{CMO}^{RLMO} \quad \text{(formula 14)}$$

The fragment-added molecular orbital computing section 113 computes MO in the case where fragments are added to a starting cluster. The computation for determining molecular electronic states is executed by e.g. solving a Fock matrix by a self-consistent field (SCF) method in the similar manner as the background art.

The input section 12 is a device with which various commands including computation start designation to the molecular orbital computing device 1, structural data, and various data including initial electron density are inputted. The input section 12 may include e.g. a keyboard, a mouse, and the like. The output section 13 is a device through which commands and data entered through the input section 12, computation results of the molecular orbital computing device 1, and the like are outputted. The output section 13 may include e.g. display devices such as a CRT display, an LCD, an organic light emitting display, and a plasma display, and printing devices such as a printer.

The internal storage 14 is a so-called working memory for reading a molecular orbital computing program or a control program to be executed by the computing processor 11 from the auxiliary storage 16, and for temporarily storing individual data which are generated during execution of the molecular orbital computing program. The internal storage 14 may include e.g. an RAM (random access memory), which is a volatile storage device.

The auxiliary storage 16 may include e.g. a nonvolatile storage device such as an ROM and an EEPROM, and a device such as a hard disk device for storing data or programs. The auxiliary storage 16 stores therein various programs (not shown) including a molecular orbital computing program for computing molecular orbitals according to the invention, and a control program for operating the molecular orbital computing device 1, as well as data (not shown) including data concerning initial electron density $D_{initial}$, which are required in executing the programs.

The computing processor 11, the input section 12, the output section 13, the internal storage 14, and the auxiliary storage 16 are respectively connected to the bus 18 to interactively exchange the data.

The molecular orbital computing device 1 may further include an external storage 15 and a communication interface section 17 indicated by the broken lines in FIG. 1.

The external storage 15 is e.g. a device with which data is read from and/or written into a recording medium such as a flexible disk, a CD-ROM (compact disc read only memory), a CD-R (compact disc recordable), and a DVD-R (digital versatile disc recordable), and may include a flexible disk drive, a CD-ROM drive, a CD-R drive, and a DVD-R drive. The communication interface section 17 is a device to be connected to a network for communicating communication signals with other servers, other user terminals, or the like via the network.

In the case where the programs are not stored, the programs may be installed from a recording medium recorded with the programs to the auxiliary storage 16 via the external storage 15. Alternatively, the programs may be downloaded from a server (not shown) administering the programs via the network and the communication interface section 17. Also, the molecular orbital computing device 1 may be configured in such a manner that data to be inputted to the molecular orbital computing device 1 in computing the molecular orbitals are inputted to the molecular orbital computing device 1 via the external storage 15, with use of a recording medium recorded with the data. Alternatively, the data may be entered to the molecular orbital computing device 1 by the user via the network and the communication interface section 17.

Next, an operation of the embodiment is described.

Operation of Embodiment

First, a coordinate system is determined with respect to an object whose molecular orbitals are to be calculated, and structural data of a starting cluster is created based on the determined coordinate system. Then, the structural data is inputted to the molecular orbital computing device 1 via the input section 12, and a designation to start molecular orbital computation is inputted to the molecular orbital computing device 1 via the input section 12. The structural data is coordinate data, concerning the atoms constituting the starting cluster, based on the determined coordinate system.

FIG. 3 is a flowchart showing an operation of the molecular orbital computing device by the elongation method. Referring to FIG. 3, in response to the input of the structural data of the starting cluster and the computation start designation, the molecular orbital computing section 111 of the computing processor 11 computes CMOs by AO basis of the starting cluster, and notifies the regional localization computing section 112 of the computation result (S11).

Then, upon receiving the notification, the regional localization computing section 112 of the computing processor 11 implements a regional localization process of transforming the CMOs by AO basis of the starting cluster into RLMOs basis, by using the transformation matrix Y expressed by the aforementioned formula 13, and notifies the fragment-added molecular orbital computing section 113 of the computation result (S12). In this way, the molecular orbital computing device 1 by the elongation method according to the embodiment is operative to directly transform the CMOs by AO basis into RLMOs basis, by using the transformation matrix Y expressed by the formula 13. With this arrangement, unlike the background art, there is no need of implementing a process of: arbitrarily selecting two CMOs in pairs from the CMOs; transforming the CMOs in pairs into MO which has been respectively localized to a frozen LMO region and an active LMO region; and iteratively executing the transformation until convergence is seen with respect to all the pairs. Accordingly, a high-speed regional localization process can be executed, as compared with the localization process according to the background art. Also, this arrangement eliminates an arbitrary property, which may be generated in sorting the CMOs into MO which has been respectively localized to the frozen LMO region and the active LMO region.

Next, upon receiving the notification, the fragment-added molecular orbital computing section 113 of the computing processor 11 computes MO in the case where fragments are added to the starting cluster by solving a Fock matrix by the SCF method in the similar manner as described in the background art (S13).

Then, the fragment-added molecular orbital computing section 113 judges whether a resultant obtained by adding a fragment to the starting cluster is a targeted object for computation (S14). If the judgment result indicates that the resultant is not the computation object, the fragment-added molecular orbital computing section 113 regards the resultant in Step S13 obtained by adding the fragment to the starting cluster, as a new starting cluster, and the routine returns to Step S12 after notifying the regional localization computing section 112 of the molecular orbitals of the new starting cluster. If, on the other hand, the judgment result indicates that the resultant is the computation object, the fragment-added molecular orbital computing section 113 outputs the electronic states of the computation object to the output section 13, and the molecular orbital computation is ended. Concerning the operation from Step S12 through Step S14, which is iteratively implemented until the resultant in Step S13 obtained by adding a fragment to the starting cluster is judged to be the computation object, similarly to the background art, the frozen AO region remotely away from the active LMO region is eliminated from the calculation object by fixing the electronic states in the frozen AO region because interaction with the fragment is not acted in the frozen AO region; the computation is implemented with respect to the active AO region having a certain length; and the active AO region is successively shifted toward the other end of the resultant to which a fragment is added, each time the fragment is added.

In this way, the molecular orbital computing device 1 according to the embodiment is operative to compute molecular orbitals at a high speed, as compared with the method described in the background art, by applying the formula 13 to the localization process. Accordingly, the embodiment is advantageous in computing molecular orbitals of a giant molecule within a reasonable time, which was impossible by the method described in the background art.

As an example, a comparison result is shown concerning computation times in the case where electronic states of polyglycine produced by synthesizing twenty glycines were computed. The computations were executed by the molecular orbital computing method according to the embodiment and by the molecular orbital computing method according to the background art, wherein five glycines were used as a starting cluster, and one to fifteen glycines were successively added as fragments. A personal computer with 3 GHz Pentium Processor® as a CPU was used as the molecular orbital computing device by the elongation method.

Figure 4:
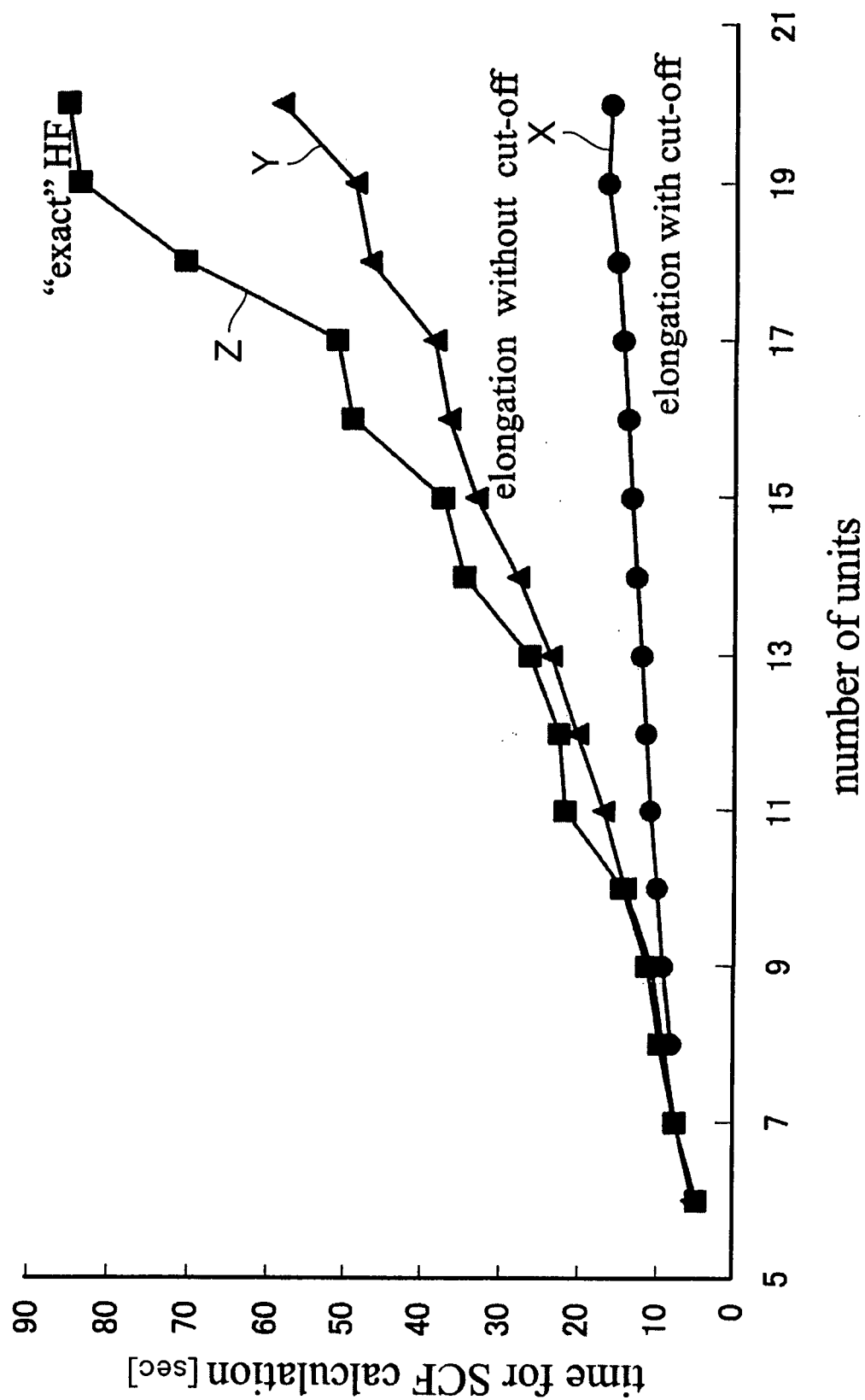
FIG. 4 is a graph showing a comparison result on computation times concerning polyglycine.

FIG. 4 is a graph showing the comparison result on computation times concerning polyglycine. In FIG. 4, the axis of abscissas shows the number of glycines as fragments, and the axis of ordinate shows an SCF calculation time in the unit of second. The broken line X shows an SCF computation time in the case where a below-mentioned cutoff process was employed, with the solid circles ● showing the respective measurement values. The broken line Y shows an SCF computation time according to the embodiment, with the solid triangles ▲ showing the respective measurement values. The broken line Z shows an SCF computation time according to the background art, with the solid rectangles ■ showing the respective measurement values.

Figure 5:
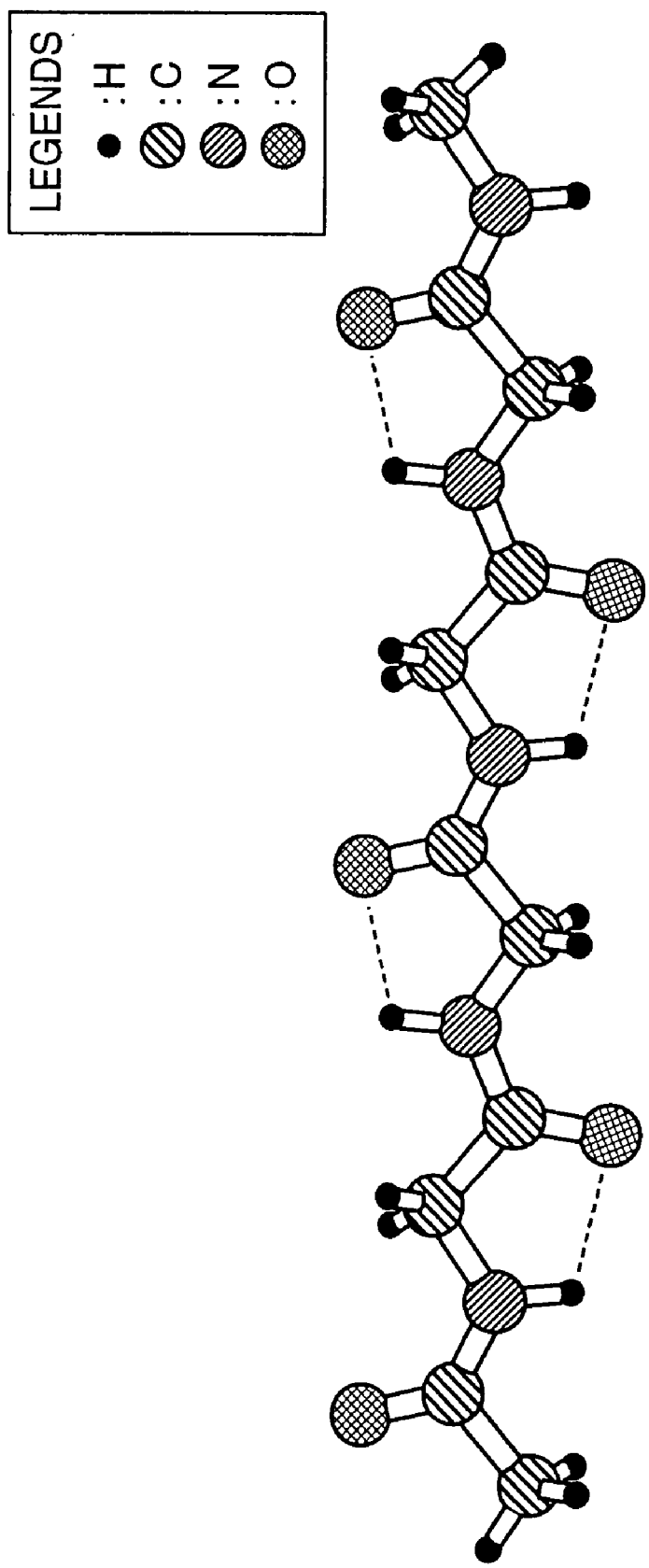
FIG. 5 is a diagram showing a molecular structure of polyglycine.

FIG. 5 is a diagram showing the molecular structure of polyglycine. The solid circles ■ represent hydrogen atoms (H), the circles ○ with leftwardly oblique lines represent carbon atoms (C), the circles ○ with rightwardly oblique lines represent nitrogen atoms (N), and the circles ○ with grid patterns represent oxygen atoms (O).

As is obvious from a comparison between the broken line Y and the broken line Z in FIG. 4, the SCF computation time according to the embodiment is short, as compared with the SCF computation time according to the background art. In other words, the molecular orbital computing device 1 by the elongation method according to the embodiment provides high-speed computation, as compared with the background art. Also, as the number of fragments is increased, the difference in SCF computation time between the embodiment and the background art is increased. Accordingly, in computing electronic states of a giant molecule, the molecular orbital computing device 1 by the elongation method according to the embodiment is advantageous, as compared with the background art.

Figure 6A:
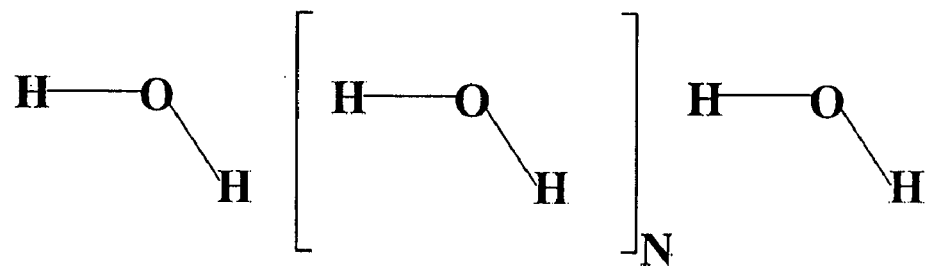
FIGS. 6A through 6C are diagrams showing chemical formulas of targeted materials for computation.

As another example, as shown in FIG. 6A, the total energies of water clusters were computed in the case where several water molecules were bonded in a chain-like manner ($H_2O$—$[H_2O]_N$—$H_2O$) by hydrogen bonding, with water molecules used as fragments. The computations were executed by the molecular orbital computing method according to the embodiment, and by the molecular orbital computing method according to the background art, wherein 6-31G was used as a basis set, five water molecules were used as a starting cluster, and one to twenty-five water molecules were successively added as fragments. Comparison results concerning the computations are shown in Table 1.

TABLE I

RHF/6-31G total energies (a.u.) of water chain obtained from conventional ($E^{cvl}$) and elongation ($E^{elg}$) calculations. The last column contains the energy differences, $\Delta E = E^{elg} - E^{cvl}$ (in $10^{-6}$ a.u.).

| Number of $H_2O$ | Conventional | Elongation | $\Delta E$ |
|---|---|---|---|
| 6 | −455.91231210 | −455.91231210 | 0.00 |
| 7 | −531.89882761 | −531.89882757 | 0.03 |
| 8 | −607.88537223 | −607.88537211 | 0.12 |
| 9 | −683.87193539 | −683.87193514 | 0.25 |
| 10 | −759.85851105 | −759.85851064 | 0.41 |
| 11 | −835.84509555 | −835.84509496 | 0.60 |
| 12 | −911.83168652 | −911.83168572 | 0.80 |
| 13 | −987.81828236 | −987.81828134 | 1.02 |
| 14 | −1063.80488197 | −1063.80488072 | 1.25 |
| 15 | −1139.79148455 | −1139.79148306 | 1.49 |
| 16 | −1215.77808951 | −1215.77808778 | 1.74 |
| 17 | −1291.76469642 | −1291.76469443 | 1.99 |
| 18 | −1367.75130493 | −1367.75130267 | 2.25 |
| 19 | −1443.73791477 | −1443.73791226 | 2.52 |
| 20 | −1519.72452575 | −1519.72452296 | 2.79 |
| 21 | −1595.71113769 | −1595.71113463 | 3.06 |
| 22 | −1671.69775045 | −1671.69774712 | 3.33 |
| 23 | −1747.68436393 | −1747.68436032 | 3.61 |
| 24 | −1823.67097803 | −1823.67097413 | 3.89 |
| 25 | −1899.65759267 | −1899.65758849 | 4.17 |
| 26 | −1975.64420779 | −1975.64420333 | 4.46 |
| 27 | −2051.63082334 | −2051.63081859 | 4.74 |
| 28 | −2127.61743926 | −2127.61743423 | 5.03 |
| 29 | −2203.60405553 | −2203.60405021 | 5.32 |
| 30 | −2279.59067209 | −2279.59066648 | 5.61 |

In Table 1, the column indicated as "Conventional" shows the total energies (unit: a.u.) of water clusters in the case computation was executed by the molecular orbital computing method according to the background art, and the column indicated as "Elongation" shows the total energies (unit: a.u.) of water clusters in the case where computation was executed by the molecular orbital computing method according to the embodiment, and the column indicated as "ΔE" shows the energy differences (unit: $10^{-6}$ a.u.) between the background art method and the embodiment method.

As is obvious from Table 1, substantially the same results are obtained concerning the computation by the molecular orbital computing method according to the embodiment, and the computation by the molecular orbital computing method according to the background art. A computation error concerning the energies, which may be generated each time one fragment is added, is on the order of 0.1 to 0.2 cal. Accordingly, it is conceived that the computation results show substantial matching.

Figure 6B:
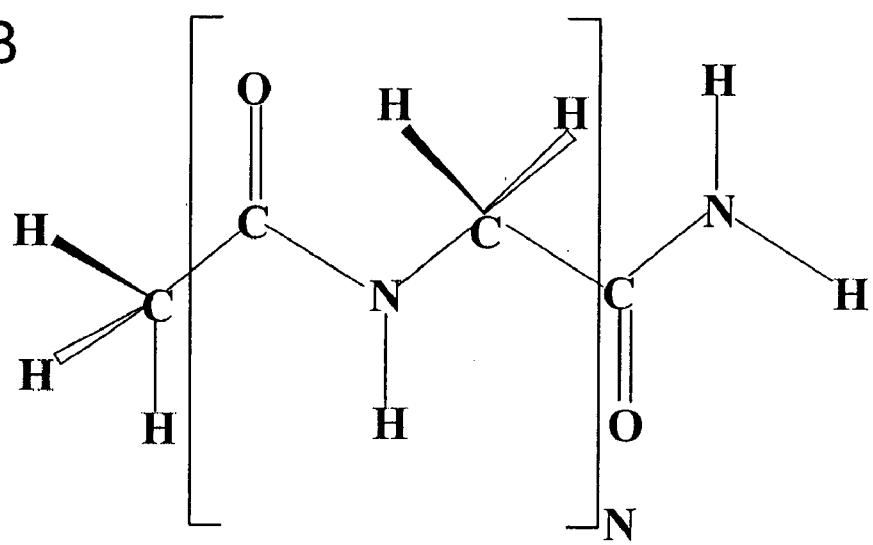

As yet another example, as shown in FIG. 6B, the total energies of polyglycine were computed, while changing the starting cluster, in synthesizing polyglycine ($CH_3$—[CO—NH—$CH_2$]NCONH$_2$) by using glycines as fragments. The computations were implemented by the molecular orbital computing method according to the embodiment, with use of STO-3G as a basis set, wherein glycines were successively added as fragments until polyglycine was synthesized based on twenty glycines, with respect to individual cases where four to eight glycines were used as the starting clusters. Comparison results concerning the computations are shown in Table 2.

TABLE II

RHF/STO-3G total energies (in a.u.) of polyglycine, as obtained from conventional calculations, and energy differences $\Delta E = E^{elg} - E^{cvl}$ (in $10^{-6}$ a.u.) for different size starting clusters ($N_{st}$). N is defined in FIG. 2.

| N | Conventional | $\Delta E$ ($N_{st}=4$) | $\Delta E$ ($N_{st}=5$) | $\Delta E$ ($N_{st}=6$) | $\Delta E$ ($N_{st}=7$) | $\Delta E$ ($N_{st}=8$) |
|---|---|---|---|---|---|---|
| 4 | −856.14997927 | 0.00 | | | | |
| 5 | −1060.26460708 | 0.13 | 0.00 | | | |
| 6 | −1264.37928877 | 0.38 | 0.16 | 0.00 | | |
| 7 | −1468.49397305 | 0.72 | 0.43 | 0.16 | 0.00 | |
| 8 | −1672.60867708 | 1.11 | 0.79 | 0.44 | 0.17 | 0.00 |
| 9 | −1876.72338190 | 1.55 | 1.20 | 0.82 | 0.45 | 0.17 |
| 10 | −2080.83809595 | 2.02 | 1.66 | 1.24 | 0.83 | 0.46 |
| 11 | −2284.95281027 | 2.51 | 2.13 | 1.70 | 1.25 | 0.84 |
| 12 | −2489.06752962 | 3.02 | 2.63 | 2.18 | 1.72 | 1.26 |
| 13 | −2693.18224908 | 3.54 | 3.15 | 2.68 | 2.20 | 1.73 |
| 14 | −2897.29697156 | 4.07 | 3.68 | 3.20 | 2.71 | 2.21 |
| 15 | −3101.41169409 | 4.61 | 4.21 | 3.73 | 3.23 | 2.72 |
| 16 | −3305.52641858 | 5.16 | 4.76 | 4.27 | 3.76 | 3.24 |
| 17 | −3509.64114310 | 5.72 | 5.31 | 4.82 | 4.30 | 3.78 |
| 18 | −3713.75586896 | 6.28 | 5.87 | 5.37 | 4.85 | 4.32 |
| 19 | −3917.87059484 | 6.84 | 6.43 | 5.93 | 5.41 | 4.87 |
| 20 | −4121.98532166 | 7.41 | 6.99 | 6.49 | 5.96 | 5.42 |

In Table 2, the column indicated as "Conventional" shows the total energies (unit: a.u.) of polyglycine in the case computation was executed by the molecular orbital computing method according to the background art, the columns indicated as "$\Delta E(N_{st}=4)$", "$\Delta E(N_{st}=5)$", "$\Delta E(N_{st}=6)$", "$\Delta E(N_{st}=7)$", and "$\Delta E(N_{st}=8)$" show the differences (unit: $10^{-6}$ a.u.) in computation results between by the molecular orbital computing method according to the embodiment, wherein four to eight glycines were used as individual starting clusters, and by the molecular orbital computing method according to the background art.

Figure 6C:
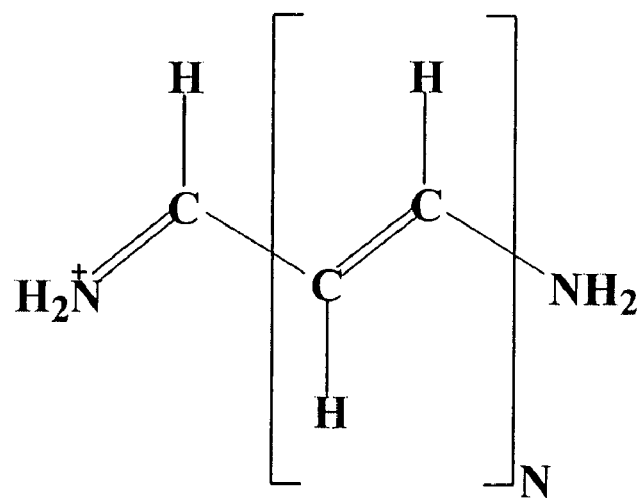

As yet another example, as shown in FIG. 6C, the total energies of cationic cyanine ($NH_2^+CH$—[$CH$=$CH$]—$NH_2$) with use of ethylenes as fragments were computed, while changing the starting cluster. The computations were implemented by the molecular orbital computing method according to the embodiment, with use of STO-3G as a basis set, wherein ethylenes were successively added as fragments until cationic cyanine was synthesized based on thirty-eight ethylenes, with respect to individual cases where ten to eighteen ethylenes, incremented by two, were used as the starting clusters. Comparison results concerning the computations are shown in Table 3.

TABLE III

RHF/STO-3G total energies (in a.u.) of cationic cyanines, as obtained from conventional calculations, and energy differences $\Delta E = E^{elg} - E^{cvl}$ (in a.u.) for different size starting clusters ($N_{st}$). N is defined in FIG. 2.

| N | Conventional | $\Delta E$ ($N_{st}$ = 10) | $\Delta E$ ($N_{st}$ = 12) | $\Delta E$ ($N_{st}$ = 14) | $\Delta E$ ($N_{st}$ = 16) | $\Delta E$ ($N_{st}$ = 18) |
|---|---|---|---|---|---|---|
| 10 | −907.0294875 | 0.000E+00 | | | | |
| 11 | −982.9678631 | 2.643E−04 | | | | |
| 12 | −1058.9060880 | 4.585E−04 | 0.000E+00 | | | |
| 13 | −1134.8442013 | 6.290E−04 | 9.618E−05 | | | |
| 14 | −1210.7822352 | 7.748E−04 | 1.563E−04 | 0.000E+00 | | |
| 15 | −1286.7202161 | 8.963E−04 | 2.052E−04 | 3.490E−05 | | |
| 16 | −1362.6581659 | 9.970E−04 | 2.441E−04 | 4.839E−05 | 0.000E+00 | |
| 17 | −1438.5961016 | 1.081E−03 | 2.749E−04 | 5.785E−05 | 1.264E−05 | |
| 18 | −1514.5340365 | 1.155E−03 | 3.002E−04 | 6.476E−05 | 1.126E−05 | 0.000E+00 |
| 19 | −1590.4719800 | 1.223E−03 | 3.229E−04 | 7.074E−05 | 9.739E−06 | 4.713E−06 |
| 20 | −1666.4099384 | 1.289E−03 | 3.452E−04 | 7.718E−05 | 8.761E−06 | −1.085E−06 |
| 21 | −1742.3479152 | 1.356E−03 | 3.687E−04 | 8.504E−05 | 9.002E−06 | −5.577E−06 |
| 22 | −1818.2859122 | 1.426E−03 | 3.945E−04 | 9.486E−05 | 1.084E−05 | −8.878E−06 |
| 23 | −1894.2239294 | 1.500E−03 | 4.230E−04 | 1.068E−04 | 1.435E−05 | −1.093E−05 |
| 24 | −1970.1619663 | 1.579E−03 | 4.544E−04 | 1.207E−04 | 1.941E−05 | −1.178E−05 |
| 25 | −2046.1000215 | 1.663E−03 | 4.887E−04 | 1.365E−04 | 2.579E−05 | −1.160E−05 |
| 26 | −2122.0380934 | 1.751E−03 | 5.255E−04 | 1.538E−04 | 3.319E−05 | −1.064E−05 |
| 27 | −2197.9761805 | 1.843E−03 | 5.648E−04 | 1.725E−04 | 4.135E−05 | −9.121E−06 |
| 28 | −2273.9142810 | 1.940E−03 | 6.062E−04 | 1.922E−04 | 5.003E−05 | −7.280E−06 |
| 29 | −2349.8523935 | 2.040E−03 | 6.495E−04 | 2.127E−04 | 5.903E−05 | −5.311E−06 |
| 30 | −2425.7905166 | 2.143E−03 | 6.944E−04 | 2.339E−04 | 6.820E−05 | −3.360E−06 |
| 31 | −2501.7286489 | 2.250E−03 | 7.408E−04 | 2.556E−04 | 7.744E−05 | −1.538E−06 |
| 32 | −2577.6667893 | 2.359E−03 | 7.886E−04 | 2.778E−04 | 8.670E−05 | 8.390E−08 |
| 33 | −2653.6049368 | 2.471E−03 | 8.374E−04 | 3.004E−04 | 9.590E−05 | 1.461E−06 |
| 34 | −2729.5430905 | 2.584E−03 | 8.874E−04 | 3.233E−04 | 1.050E−04 | 2.574E−06 |
| 35 | −2805.4812496 | 2.700E−03 | 9.382E−04 | 3.465E−04 | 1.141E−04 | 3.423E−06 |
| 36 | −2881.4194135 | 2.817E−03 | 9.899E−04 | 3.700E−04 | 1.231E−04 | 4.026E−06 |
| 37 | −2957.3575815 | 2.936E−03 | 1.042E−03 | 3.937E−04 | 1.320E−04 | 4.394E−06 |
| 38 | −3033.2957532 | 3.056E−03 | 1.095E−03 | 4.176E−04 | 1.409E−04 | 4.553E−06 |

Similarly to Table 2, in Table 3, the column indicated as "Conventional" shows the total energies (unit: a.u.) of cationic cyanine in the case computation was executed by the molecular orbital computing method according to the background art, the columns indicated as "$\Delta E(N_{st}=10)$", "$\Delta E(N_{st}=12)$", "$\Delta E(N_{st}=14)$", "$\Delta E(N_{st}=16)$", and "$\Delta E(N_{st}=18)$" show the differences (unit: $10^{-6}$ a.u.) in computation results between by the molecular orbital computing method according to the embodiment, wherein four to eight glycines were used as individual starting clusters, and by the molecular orbital computing method according to the background art.

As is obvious from Table 2 and Table 3, as the size (length) of the starting cluster is increased, the difference in computation result between by the molecular orbital computing method according to the embodiment and by the molecular orbital computing method according to the background art is decreased. Concerning polyglycine (see Table 2), the computation error has substantially no difference with respect to all the cases of using the starting clusters ($N_{st}$)=4 through 8, and the computation results show substantial matching. However, concerning cationic cyanine, the matching rate is increased, as $N_{st}$ is increased. This shows that the latter model is a conjugation system, and a large starting cluster is required due to non-localization of $\pi$ electrons.

In the foregoing embodiment, the SCF computation in the molecular orbital computation process after fragment addition in Step S13 may include a cut-off process of partially cutting off two-electron integral (rs|tu) computation in creating a Fock matrix to further increase the computation speed.

Specifically, concerning a two-electron integral (rs|tu) of an active AO region, defining: $r'=r-n_A$, $s'=s-n_A$, $t'=t-n_A$, $u'=u-n_A$ ($n_A$ is the number of a terminal segment of a frozen orbital), the range satisfying the formula 15-1 and the formula 15-2 is approximated to 0, and the range satisfying the formula 15-3 through the formula 15-5 is computed:

$$r',s',t',u' \leq 0 \quad \text{(formula 15-1)}$$

$$r'>0, \text{ and } s',t',u' \leq 0 \quad \text{(formula 15-2)}$$

$$r',s'>0, \text{ and } t',u' \leq 0 \quad \text{(formula 15-3)}$$

$$t'>0, \text{ and } r',u' \leq 0 \quad \text{(formula 15-4)}$$

$$r',s',t'>0, \text{ and } u' \leq 0 \quad \text{(formula 15-5)}$$

Then, a coulomb term and an exchange term are computed concerning a two-electron integral (rs|tu) between respective fragments of the active AO region and a fragment to be added; and a coulomb term is computed concerning a two-electron integral (rs|tu) between a frozen AO region and a fragment to be added.

The density matrix $D_{Total}$ by AO basis after the cut-off process is expressed by the formula 16.

$$D_{Total}=D_1 \$ D \quad \text{(formula 16)}$$

Here, $D_1$ is the density matrix of the starting cluster (including a starting cluster, which is defined as a new starting cluster by fragment addition in the iterative calculation), $D_{current}$ is the density matrix of the active AO region to which a fragment is added, and $\delta D$ is a contributory factor to the density matrix in the frozen AO region. In the example of FIG. 11(E), $D_1$ is expressed by the formula 16-1, D is expressed by the formula 16-2, and B is each fragment in a localized region in the formulas 16-1, 16-2, 17-2, and 17-3, and is $A_4$, $A_5$, and $A_6$.

$$D_1 = D_1(A_1, A_2, A_3, B) \quad \text{(formula 16-1)}$$
$$\approx D_1(A_1, A_2, A_3, B, M)$$
$$\approx D_1(A_1, A_2, A_3)$$

$$D = D_{Current}(A_2, A_3, B, M) + \delta D(A_1) \quad \text{(formula 16-2)}$$

Also, the total energy $E_{Total}$ by AO basis after the cut-off process is expressed by the formula 17.

$$W_{Total} = 0.5 \times Tr(E_{Total} D_{1\,Total}) \quad \text{(formula 17)}$$

where $W_{Total}$ is expressed by the formula 17-1, $W_1$ is the total energy of the starting cluster (including a starting cluster, which is defined as a new starting cluster by fragment addition in the iterative calculation), $W_{Current}$ is the total energy of the active AO region after fragment addition, $\delta W$ is a contributory factor to the total energy in the frozen AO region. In the example of FIG. 11(E), $W_1$ is expressed by the formula 17-2, and W is expressed by the formula 17-3.

$$W_{Total} = W_1 \$ W \quad \text{(formula 17-1)}$$

$$W_1 = W_1(A_1, A_2, A_3, B) + \delta W_1(A_1 - M) \quad \text{(formula 17-2)}$$

$$W = W_{Current}(A_2, A_3, B, M) + \delta D[A_1 - (A_2, A_3, B, M)] \quad \text{(formula 17-3)}$$

The operation in Step S13 can be processed as follows by implementing the above-mentioned cut-off process.

Figure 7:
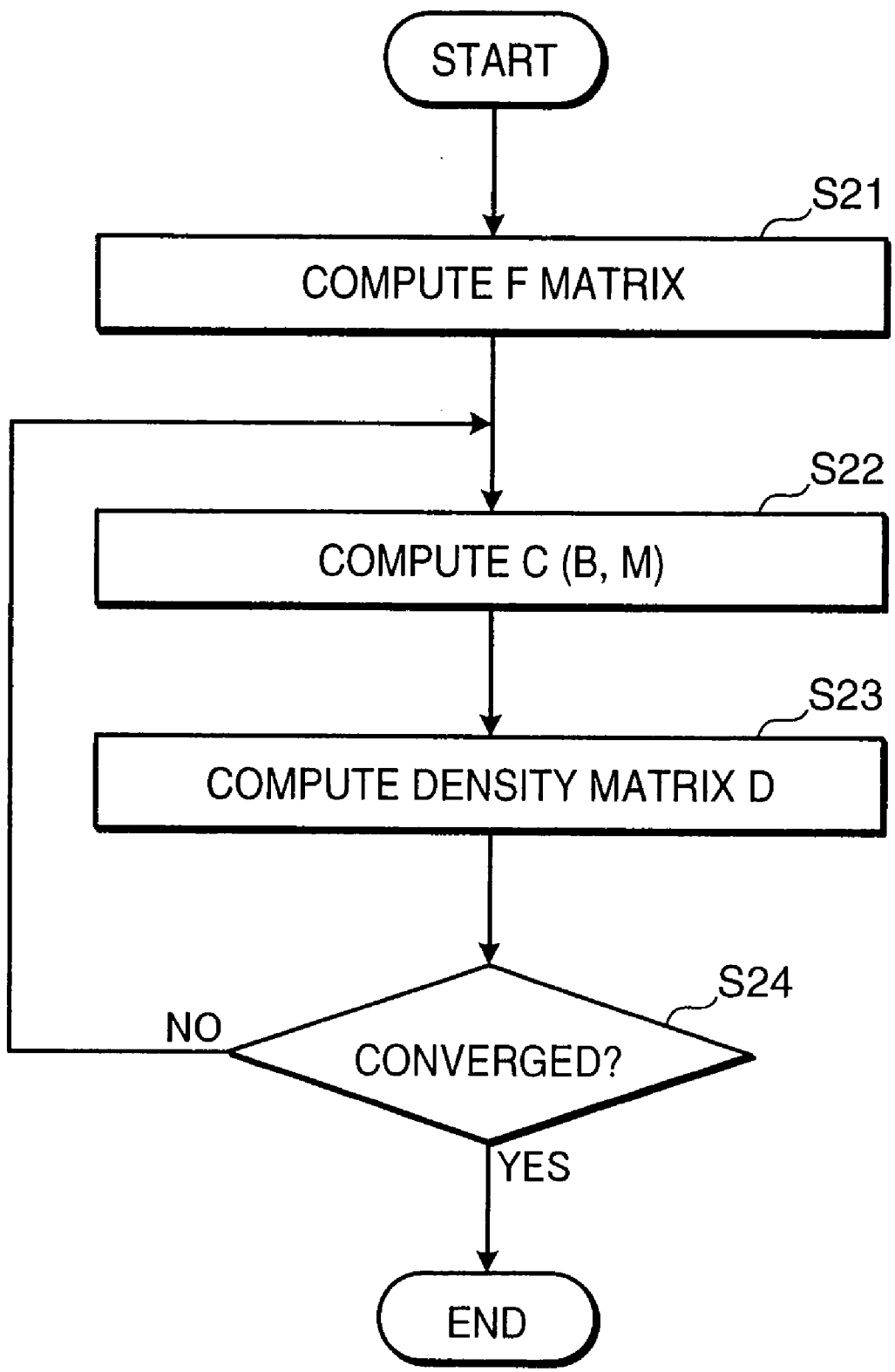
FIG. 7 is a flowchart showing a molecular orbital computation process after fragment addition in implementing a cut-off process.
Figure 10A:
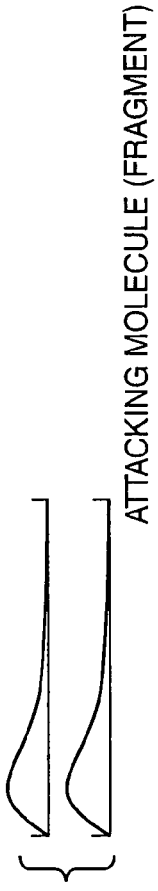
FIGS. 10A through 10C are diagrams for describing computations in adding fragments to active LMOs.
Figure 10B:
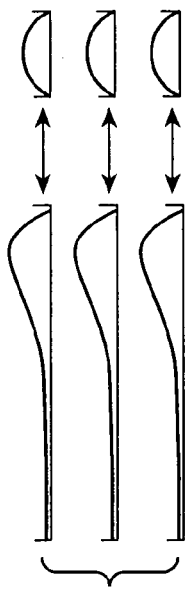
Figure 10C:
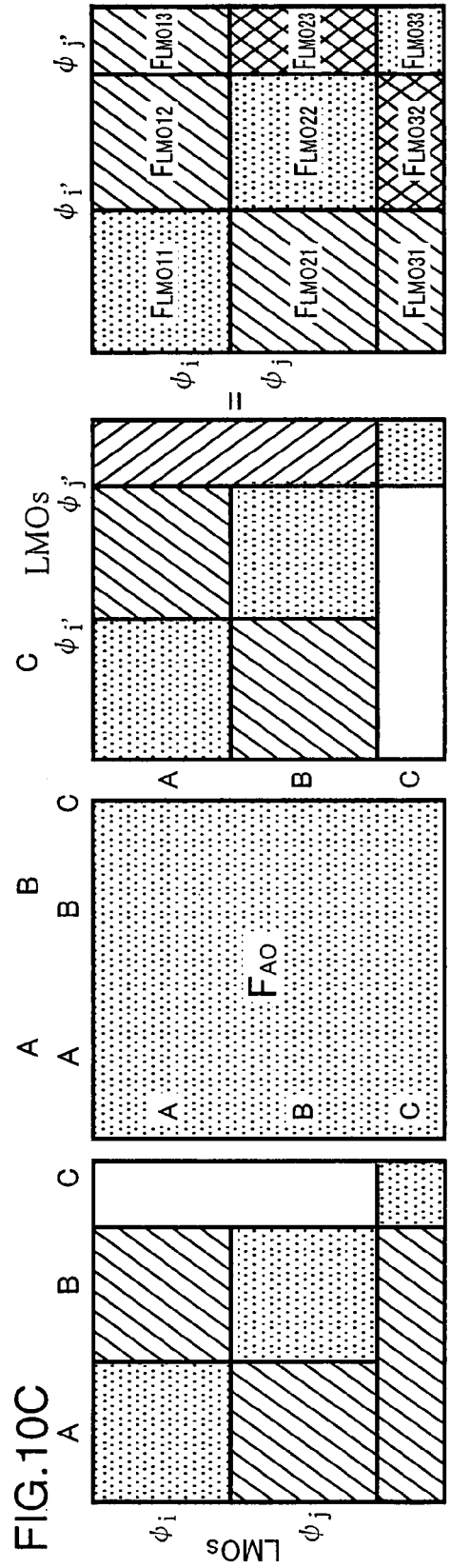

FIG. 7 is a flowchart showing a molecular orbital computation process after fragment addition in implementing the cut-off process.

Referring to FIG. 7, first, the fragment-added molecular orbital computing section 113 computes the F matrix, by using the initial density matrix $D_{initial}$ (S21). Then, the fragment-added molecular orbital computing section 113 computes the canonical molecular orbital C (B, M) in the case where a fragment is added (S22). Then, the fragment-added molecular orbital computing section 113 computes the density matrix D e.g. the density matrix D expressed by the formula 16-2 (S23). Then, the fragment-added molecular orbital computing section 113 judges whether the density matrix D is converged (S24). If the judgment result indicates non-convergence (No in Step S24), the fragment-added molecular orbital computing section 113 returns the process to Step S21. If, on the other hand, the judgment result indicates convergence (Yes in Step S24), the fragment-added molecular orbital computing section 113 terminates the molecular orbital computation process after the fragment addition.

If the judgment result in Step S14 indicates that the resultant is the targeted polymer, the fragment-added molecular orbital computing section 113 computes $D_{Total}$ and $W_{Total}$, by using the computation results obtained in Steps S21 through S24, and computes $E_{Total}$.

As mentioned above, by introducing the cut-off process, the molecular orbital computing device 1 according to the embodiment is capable of computing molecular orbitals at a high speed, as compared with the case where the background art method is employed. Accordingly, the embodiment is advantageous in computing molecular orbitals of a giant molecule within a reasonable time, which was impossible by the method described in the background art.

For instance, as is obvious from the comparison between the broken line X, and the broken lines Y and Z in FIG. 4, the SCF computation time in the case where the cut-off process is introduced is shorter than the SCF computation time in the case where the background art method is employed. Further, the SCF computation time in the case where the cut-off process is introduced is shorter than the SCF computation time in the case where the aforementioned formula 13 is employed. In other words, the molecular orbital computing device 1 by the elongation method according to the embodiment, with introduction of the cut-off process, is advantageous in providing high-speed computation, as compared with the case where the background art method is employed, and the case where the formula 13 is employed. Also, as the number of fragments is increased, the difference in SCF computation time between the embodiment with introduction of the cut-off process, and the background art is considerably large. Accordingly, in computing electronic states of a giant molecule, the molecular orbital computing device 1 by the elongation method according to the embodiment is effectively advantageous, as compared with the background art.

As still another example, the total energies of polyglycine were computed, while changing the starting cluster, in synthesizing polyglycine ($CH_3$—[CO—NH—$CH_2$N] CO—$NH_2$) by using glycines as fragments. The computations were implemented by a molecular orbital computing method with introduction of the cut-off process, and by a molecular orbital computing method, in which solely a regional localization process was executed without execution of the cut-off process, with use of STO3G as a basis set, wherein glycines were successively added as fragments until polyglycine was synthesized based on twenty glycines, with respect to individual cases where five glycines and nine glycines were used as the starting clusters. Comparison results concerning the computations are shown in Table 4.

TABLE 4

RHF/STO-3G total energies (a.u.) for C5 conformer of polyglycine obtained from "exact" HF and from elongation calculations with and without cut-off. Two different size starting clusters are used.

| | | Elongation $N_{st} = 5$ | | Elongation $N_{st} = 9$ | |
|---|---|---|---|---|---|
| N | "Exact" | No cut-off | cut-off | No cut-off | cut-off |
| 6 | −1264.3792888 | −1264.3792887 | | | |
| 7 | −1468.4939730 | −1468.4939730 | | | |
| 8 | −1672.6086771 | −1672.6086770 | | | |
| 9 | −1876.7233819 | −1876.7233818 | | | |

TABLE 4-continued

RHF/STO-3G total energies (a.u.) for C5 conformer of polyglycine obtained from "exact" HF and from elongation calculations with and without cut-off. Two different size starting clusters are used.

| | | Elongation $N_{st} = 5$ | | Elongation $N_{st} = 9$ | |
|---|---|---|---|---|---|
| N | "Exact" | No cut-off | cut-off | No cut-off | cut-off |
| 10 | −2080.8380959 | −2080.8380958 | −2080.8380960 | −2080.8380959 | |
| 11 | −2284.9528103 | −2284.9528101 | −2284.9528103 | −2284.9528103 | |
| 12 | −2489.0675296 | −2489.0675294 | −2489.0675296 | −2489.0675297 | −2489.0675296 |
| 13 | −2693.1822491 | −2693.1822488 | −2693.1822490 | −2693.1822492 | −2693.1822491 |
| 14 | −2897.2969716 | −2897.2969712 | −2897.2969715 | −2897.2969717 | −2897.2969716 |
| 15 | −3101.4116941 | −3101.4116936 | −3101.4116940 | −3101.4116943 | −3101.4116941 |
| 16 | −3305.5264186 | −3305.5264180 | −3305.5264185 | −3305.5264188 | −3305.5264186 |
| 17 | −3509.6411431 | −3509.6411425 | −3509.6411430 | −3509.6411434 | −3509.6411431 |
| 18 | −3713.7558690 | −3713.7558683 | −3713.7558688 | −3713.7558692 | −3713.7558689 |
| 19 | −3917.8705948 | −3917.8705940 | −3917.8705946 | −3917.8705952 | −3917.8705948 |
| 20 | −4121.9853217 | −4121.9853208 | −4121.9853214 | −4121.9853220 | −4121.9853216 |

In Table 4, the column indicated as "Exact" shows the total energies (unit: a.u.) of polyglycine in the case computation was executed with respect to all the systems by a molecular orbital computing method according to the background art, the columns indicated as "Elongation ($N_{st}$=5)" and "Elongation ($N_{st}$=9)" show computation results concerning the cases where five glycines and nine glycines were used as starting clusters. In each of the columns "Elongation ($N_{st}$=5)" and "Elongation ($N_{st}$=9)", computation results (No cut-off) by the molecular orbital computing method, in which solely the regional localization process was executed without execution of the cut-off process, and computation results (cut-off) by the molecular orbital computing method with introduction of the cut-off process are shown.

As is obvious from Table 4, as the size (length) of the starting cluster is increased, the computation results by the molecular orbital computing method with introduction of the cut-off process show substantial matching with the exact energy values. Also, the computation results are substantially the same as the computation results obtained by the molecular orbital computing method, in which solely the regional localization process was executed without execution of the cut-off process.

The following is a brief summary on the invention disclosed in the specification.

A molecular orbital computing device by an elongation method for determining molecular electronic states by the elongation method, according to an aspect of the invention comprises: a regional localization computing section for implementing a localization process of transforming a canonical molecular orbital by an atomic orbital basis into a regional localized molecular orbital, by using the formulas expressed by the aforementioned formulas 13 and 14, where $Y_{CMO}^{RLMO}$ is a transformation matrix for transforming into a regional localized molecular orbital by a canonical molecular orbital basis, $C_{RO}^{CMO+}$ is a transpose matrix of a matrix representing a canonical molecular orbital by a regional atomic orbital basis, U is a transformation matrix for erasing elements in an off-diagonal block in a density matrix $D^{RO}$ by the regional atomic orbital basis by a Jacobi method, $C_{AO}^{RLMO}$ is a matrix representing a regional localized molecular orbital by the atomic orbital basis, and $C_{AO}^{CMO}$ is a matrix representing the canonical molecular orbital by the atomic orbital basis.

A molecular orbital computing method by an elongation method for determining molecular electronic states by the elongation method, according to another aspect of the invention, comprises: a regional localization step of implementing a localization process of transforming a canonical molecular orbital by an atomic orbital basis into a regional localized molecular orbital, by using the formulas expressed by the formulas 13 and 14, where $Y_{CMO}^{RLMO}$ is a transformation matrix for transforming into a regional localized molecular orbital by a canonical molecular orbital basis, $C_{RO}^{CMO+}$ is a transpose matrix of a matrix representing a canonical molecular orbital by a regional atomic orbital basis, U is a transformation matrix for erasing elements in an off-diagonal block in a density matrix $D^{RO}$ by the regional atomic orbital basis by a Jacobi method, $C_{AO}^{RLMO}$ is a matrix representing a regional localized molecular orbital by the atomic orbital basis, and $C_{AO}^{CMO}$ is a matrix representing the canonical molecular orbital by the atomic orbital basis.

A molecular orbital computing program by an elongation method for causing a computer to implement a computation to determine molecular electronic states by the elongation method, according to yet another aspect of the invention, comprises a regional localization step of implementing a localization process of transforming a canonical molecular orbital by an atomic orbital basis into a regional localized molecular orbital, by using the formulas expressed by the formulas 13 and 14, where $Y_{RO}^{CMO+}$ is a transformation matrix for transforming into a regional localized molecular orbital by a canonical molecular orbital basis, $C_{RO}^{CMO+}$ is a transpose matrix of a matrix representing a canonical molecular orbital by a regional atomic orbital basis, U is a transformation matrix for erasing elements in an off-diagonal block in a density matrix $D^{RO}$ by the regional atomic orbital basis by a Jacobi method, $C_{AO}^{RLMO}$ is a matrix representing a regional localized molecular orbital by the atomic orbital basis, and $C_{AO}^{CMO}$ is a matrix representing the canonical molecular orbital by the atomic orbital basis.

A computer-readable recording medium recorded with a molecular orbital computing program by an elongation method for causing a computer to implement a computation to determine molecular electronic states by the elongation method, according to a further aspect of the invention, comprises a regional localization step of implementing a localization process of transforming a canonical molecular orbital by an atomic orbital basis into a regional localized molecular orbital, by using the formulas expressed by the formulas 13 and 14, where $Y_{CMO}^{RLMO}$ is a transformation matrix for transforming into a regional localized molecular orbital by a canonical molecular orbital basis, $C_{RO}^{CMO+}$ is a transpose matrix of a matrix representing a canonical molecular orbital by a regional atomic orbital basis, U is a transformation matrix for erasing elements in an off-diagonal block in a density matrix $D^{RO}$ by the regional atomic orbital basis by a Jacobi method, $C_{AO}^{RLMO}$ is a matrix representing the regional localized molecular orbital by the atomic orbital basis, and $C_{AO}^{CMO}$ is a matrix representing the canonical molecular orbital by the atomic orbital basis.

In the molecular orbital computing device by the elongation method, the molecular orbital computing method by the elongation method, the molecular orbital computing program by the elongation method, and the recording medium recorded with the molecular orbital computing program by the elongation method constructed as mentioned above, the localization process of directly transforming the canonical molecular orbital by the atomic orbital basis into the canonical molecular orbital of the regional localized molecular orbital basis is implemented, by using the formulas expressed by the formulas 13 and 14. Unlike the background art, this eliminates the need of a process of: arbitrarily selecting two CMOs in pairs from the CMOs; transforming the CMOs in pairs into MO which has been respectively localized to a frozen LMO region and an active LMO region; and iteratively executing the transformation until convergence is seen with respect to all the pairs. With this arrangement, a high-speed regional localization process can be executed, as compared with the localization process according to the background art. Also, this arrangement eliminates an arbitrary property, which may be generated in sorting the CMOs into MO which has been respectively localized to the frozen LMO region and the active LMO region.

There is room for improvement concerning the molecular orbital computing device by the elongation method, the molecular orbital computing method by the elongation method, and the molecular orbital computing program by the elongation method in the aspect of shortening the calculation time. In view of this, preferably, in the molecular orbital computing device by the elongation method, the molecular orbital computing method by the elongation method, the molecular orbital computing program by the elongation method, and the recording medium recorded with the molecular orbital computing program by the elongation method, in creating a Fock matrix in computation by a self-consistent field method, a cut-off process is executed: concerning a two-electron integral (rs|tu) of an active AO region, defining: $r'=r-n_A$, $s'=s-n_A$, $t'=t-n_A$, $u'=u-n_A$ ($n_A$ is the number of a terminal segment of a frozen orbital), a range satisfying: $r'$, $s'$, $t'$, $u'\leq 0$, and a range satisfying: $r'>0$, and $s'$, $t'$, $u'\leq 0$ are approximated to 0, and a range satisfying: $r'$, $s'>0$, and $t'$, $u'\leq 0$, and a range satisfying: $t'>0$, and $r'$, $u'\leq 0$, and a range satisfying: $r'$, $s'$, $t'>0$, and $u'\leq 0$ are computed; concerning a two-electron integral (rs|tu) between respective fragments of the active AO region and a fragment to be added, a coulomb term and an exchange term are computed; and concerning a two-electron integral (rs|tu) between a frozen AO region and a fragment to be added, a coulomb term is computed.

In the above arrangement, in creating the Fock matrix in computation by the self-consistent field method, the cut-off process is executed: concerning the two-electron integral (rs|tu) of the active AO region, defining: $r'=r-n_A$, $s'=s-n_A$, $t'=t-n_A$, $u'=u-n_A$ ($n_A$ is the number of the terminal segment of the frozen orbital), the range satisfying: $r'$, $s'$, $t'$, $u'\leq 0$, and the range satisfying: $r'>0$, and $s'$, $t'$, $u'\leq 0$ are approximated to 0, and the range satisfying: $r'$, $s'>0$, and $t'$, $u'\leq 0$, and the range satisfying: $t'>0$, and $r'$, $u'\leq 0$, and the range satisfying: $r'$, $s'$, $t'>0$, and $u'\leq 0$ are computed; concerning the two-electron integral (rs|tu) between respective fragments of the active AO region and the fragment to be added, the coulomb term and the exchange term are computed; and concerning the two-electron integral (rs|tu) between the frozen AO region and the fragment to be added, the coulomb term is computed. This arrangement enables to execute the SCF method while omitting calculation which does not substantially contribute to the computation results. Accordingly, this arrangement is advantageous in executing the SCF method with a high speed, as compared with the background art.

Also, there is room for improvement in the aspect of shortening the calculation time in the case where the SCF method is applied in a simplified manner to solve an HFR equation in determining molecular electronic states by the elongation method.

In view of the above, a molecular orbital computing device by an elongation method for determining molecular electronic states by applying a self-consistent field method to the elongation method, according to another aspect of the invention, has the following feature. Specifically, in creating a Fock matrix in computation by the self-consistent field method, a cut-off process is executed: concerning a two-electron integral (rs|tu) of an active AO region, defining: $r'=r-n_A$, $s'=s-n_A$, $t'=t-n_A$, $u'=u-n_A$ ($n_A$ is the number of a terminal segment of a frozen orbital), a range satisfying: $r'$, $s'$, $t'$, $u'\leq 0$, and a range satisfying: $r'>0$, and $s'$, $t'$, $u'\leq 0$ are approximated to 0, and a range satisfying: $r'$, $s'>0$, and $t'$, $u'\leq 0$, and a range satisfying: $t'>0$, and $r'$, $u'\leq 0$, and a range satisfying: $r'$, $s'$, $t'>0$, and $u'\leq 0$ are computed; concerning a two-electron integral (rs|tu) between respective fragments of the active AO region and a fragment to be added, a coulomb term and an exchange term are computed; and concerning a two-electron integral (rs|tu) between a frozen AO region and a fragment to be added, a coulomb term is computed.

A molecular orbital computing method by an elongation method for determining molecular electronic states by applying a self-consistent field method to the elongation method, according to yet another aspect of the invention, has the following feature. Specifically, in creating a Fock matrix in computation by the self-consistent field method, a cut-off process is executed: concerning a two-electron integral (rs|tu) of an active AO region, defining: $r'=r-n_A$, $s'=s-n_A$, $t'=t-n_A$, $u'=u-n_A$ ($n_A$ is the number of a terminal segment of a frozen orbital), a range satisfying: $r'$, $s'$, $t'$, $u'\leq 0$, and a range satisfying: $r'>0$, and $s'$, $t'$, $u'\leq 0$ are approximated to 0, and a range satisfying: $r'$, $s'>0$, and $t'$, $u'\leq 0$, and a range satisfying: $t'>0$, and $r'$, $u'\leq 0$, and a range satisfying: $r'$, $s'$, $t'>0$, and $u'\leq 0$ are computed; concerning a two-electron integral (rs|tu) between respective fragments of the active AO region and a fragment to be added, a coulomb term and an exchange term are computed; and concerning a two-electron integral (rs|tu) between a frozen AO region and a fragment to be added, a coulomb term is computed.

A molecular orbital computing program by an elongation method for causing a computer to implement a computation to determine molecular electronic states by applying a self-consistent field method to the elongation method, according to a further aspect of the invention, has the following feature. Specifically, in creating a Fock matrix in computation by the self-consistent field method, a cut-off process is executed: concerning a two-electron integral (rs|tu) of an active AO region, defining: $r'=r-n_A$, $s'=s-n_A$, $t'=t-n_A$, $u'=u-n_A$ ($n_A$ is the number of a terminal segment of a frozen orbital), a range satisfying: $r'$, $s'$, $t'$, $u'\leq 0$, and a range satisfying: $r'>0$, and $s'$, $t'$, $u'\leq 0$ are approximated to 0, and a range satisfying: $r'$, $s'>0$, and $t'$, $u'\leq 0$, and a range satisfying: $t'>0$, and $r'$, $u'\leq 0$, and a range satisfying: $r'$, $s'$, $t'>0$, and $u'\leq 0$ are computed; concerning a two-electron integral (rs|tu) between respective fragments of the active AO region and a fragment to be added, a coulomb term and an exchange term are computed; and concerning a two-electron integral (rs|tu) between a frozen AO region and a fragment to be added, a coulomb term is computed.

A computer-readable recording medium recorded with a molecular orbital computing program by an elongation method for causing a computer to implement a computation to determine molecular electronic states by applying a self-consistent field method to the elongation method, according to yet another aspect of the invention, has the following feature. Specifically, in creating a Fock matrix in computation by the self-consistent field method, a cut-off process is executed: concerning a two-electron integral (rs|tu) of an active AO region, defining: r'=r−$n_A$, s'=s−$n_A$, t'=t−$n_A$, u'=u−$n_A$ ($n_A$ is the number of a terminal segment of a frozen orbital), a range satisfying: r', s', t', u'≦0, and a range satisfying: r'>0, and s', t', u'≦0 are approximated to 0, and a range satisfying: r', s'>0, and t', u'≦0, and a range satisfying: t'>0, and r', u'≦0, and a range satisfying: r', s', t'>0, and u'≦0 are computed; concerning a two-electron integral (rs|tu) between respective fragments of the active AO region and a fragment to be added, a coulomb term and an exchange term are computed; and concerning a two-electron integral (rs|tu) between a frozen AO region and a fragment to be added, a coulomb term is computed.

In the molecular orbital computing device by the elongation method, the molecular orbital computing method by the elongation method, the molecular orbital computing program by the elongation method, and the recording medium recorded with the molecular orbital computing program by the elongation method as mentioned above, in creating the Fock matrix in computation by the self-consistent field method, the cut-off process is executed: concerning the two-electron integral (rs|tu) of the active AO region, defining: r'=r−$n_A$, s'=s−$n_A$, t'=t−$n_A$, u'=u−$n_A$ ($n_A$ is the number of a terminal segment of a frozen orbital), the range satisfying: r', s', t', u'≦0, and the range satisfying: r'>0, and s', t', u'≦0 are approximated to 0, and the range satisfying: r', s'>0, and t', u'≦0, and the range satisfying: t'>0, and r', u'≦0, and the range satisfying: r', s', t'>0, and u'≦0 are computed; concerning the two-electron integral (rs|tu) between respective fragments of the active AO region and the fragment to be added, the coulomb term and the exchange term are computed; and concerning the two-electron integral (rs|tu) between the frozen AO region and the fragment to be added, the coulomb term is computed. This arrangement enables to execute the SCF method while omitting calculation which does not substantially contribute to the computation results. Accordingly, this arrangement is advantageous in executing the SCF method with a higher speed.

Although the present invention has been adequately and fully described by way of embodiment with reference to the accompanying drawings to express the present invention, it is to be understood that various changes and/or modifications will be apparent to those skilled in the art. Therefore, unless otherwise such changes or modifications to be implemented by those skilled in the art depart from the scope of the present invention hereinafter defined, they should be construed as being included therein.

INDUSTRIAL APPLICABILITY

According to the invention, provided are a molecular orbital computing device, by an elongation method, capable of performing an analysis on molecular electronic states at a higher speed by an ab initio molecular orbital method, a molecular orbital computing method by an elongation method, a molecular orbital computing program by an elongation method, and a recording medium recorded with the molecular orbital computing program by the elongation method.

The invention claimed is:
1. A molecular orbital computing device for determining molecular electron states by an elongation method, the device comprising:
   a processor;
   a program that causes the processor to input structural data of a starting cluster which is a part of a targeted polymer whose electronic states are to be calculated;
   the program causes the processor to output a computational result;
   a storage that stores a transformation matrix $Y_{CMO}^{RLMO}$ for transforming an orbital to be transformed into a regional localized molecular orbital by a canonical molecular orbital basis, a transpose matrix $C_{RO}^{CMO+}$ of a matrix representing a canonical molecular orbital by a regional atomic orbital basis, and a transformation matrix U for erasing elements in an off-diagonal block in a density matrix $D^{RO}$ by the regional atomic orbital basis by a Jacobi method;
   the program causes the processor to compute a canonical molecular orbital by the atomic orbital basis of the starting cluster by a predetermined molecular orbital computation method;
   the program causes the processor to implement a localization process of transforming a canonical molecular orbital by an atomic orbital basis in the starting cluster into a regional localized molecular orbital, by using the formulas expressed by:

$$Y_{CMO}^{RLMO} = C_{RO}^{CMO\dagger} U$$

$$C_{AO}^{RLMO} = C_{AO}^{CMO} Y_{CMO}^{RLMO}$$

where $Y_{CMO}^{RLMO}$ is a transformation matrix for transforming into a regional localized molecular orbital by a canonical molecular orbital basis, $C_{RO}^{CMO+}$ is a transpose matrix of a matrix representing a canonical molecular orbital by a regional atomic orbital basis, U is a transformation matrix for erasing elements in an off-diagonal block in a density matrix $D^{RO}$ by the regional atomic orbital basis by a Jacobi method, $C_{AO}^{RLMO}$ is a matrix representing a regional localized molecular orbital by the atomic orbital basis, and $C_{AO}^{CMO}$ is a matrix representing the canonical molecular orbital by the atomic orbital basis, so that a frozen AO region, which is localized in such a manner that the phase of the orbital is increased on one end of the starting cluster, and an active AO region, which is localized in such a manner that the phase of the orbital is increased on the other end of the starting cluster, are created; and
   the program causes the processor to compute a molecular orbit of the starting cluster added with predetermined fragments by the elongation method by solving a Fock matrix based on the regional localized molecular orbit by a self-consistent field method, and replacing the starting cluster with the starting cluster added with the predetermined fragments as a new starting cluster in a case where the starting cluster added with the redetermined fragments is not a targeted polymer, and outputting the computed molecular orbit as the computation result in a case where the starting cluster added with the predetermined fragments is a targeted polymer.

2. A molecular orbital computing method for determining molecular electron states by an elongation method, the molecular orbital computing method comprising:
- an input step of inputting structural data of a starting cluster which is a part of a targeted polymer whose electronic states are to be calculated;
- a molecular orbital computing step of using a programmed processor to compute a canonical molecular orbital by the atomic orbital basis of the starting cluster by a predetermined molecular orbital computation method;
- a regional localization computing step of implementing a localization process of transforming a canonical molecular orbital by an atomic orbital basis in the starting cluster into a regional localized molecular orbital, by using the formulas expressed by:

$$Y_{CMO}^{RLMO} = C_{RO}^{CMO\dagger} U$$

$$C_{AO}^{RLMO} = C_{AO}^{CMO} Y_{CMO}^{RLMO}$$

where $Y_{CMO}^{RLMO}$ is a transformation matrix for transforming an orbital to be transformed into a regional localized molecular orbital by a canonical molecular orbital basis, $C_{RO}^{CMO+}$ is a transpose matrix of a matrix representing a canonical molecular orbital by a regional atomic orbital basis, U is a transformation matrix for erasing elements in an off-diagonal block in a density matrix $D^{RO}$ by the regional atomic orbital basis by a Jacobi method, $C_{AO}^{RLMO}$ is a matrix representing a regional localized molecular orbital by the atomic orbital basis, and $C_{AO}^{CMO}$ is a matrix representing the canonical molecular orbital by the atomic orbital basis, so that a frozen AO region, which is localized in such a manner that the phase of the orbital is increased on one end of the starting cluster, and an active AO region, which is localized in such a manner that the phase of the orbital is increased on the other end of the starting cluster, are created; and
- a fragment-added molecular orbital computing step of computing a molecular orbit of the starting cluster added with predetermined fragments by the elongation method by solving a Fock matrix based on the regional localized molecular orbit by a self-consistent field method, and replacing the starting cluster with the starting cluster added with the predetermined fragments as a new starting cluster in a case where the starting cluster added with the predetermined fragments is not a targeted polymer, and outputting the computed molecular orbit as the computation result to the output section in a case where the starting cluster added with the predetermined fragments is a targeted polymer.

3. A non-transitory computer-readable recording medium recorded with a molecular orbital computing program for causing a computer to implement a computation to determine molecular electron states by the elongation method, the molecular orbital computing program comprising:
- instructions that cause a processor to perform a regional localization computing step of implementing a localization process of transforming a canonical molecular orbital by an atomic orbital basis in the starting cluster into a regional localized molecular orbital, by using the formulas expressed by:

$$Y_{CMO}^{RLMO} = C_{RO}^{CMO\dagger} U$$

$$C_{AO}^{RLMO} = C_{AO}^{CMO} Y_{CMO}^{RLMO}$$

where $Y_{CMO}^{RLMO}$ is a transformation matrix for transforming an orbital to be transformed into a regional localized molecular orbital by a canonical molecular orbital basis, $C_{RO}^{CMO+}$ is a transpose matrix of a matrix representing a canonical molecular orbital by a regional atomic orbital basis, U is a transformation matrix for erasing elements in an off-diagonal block in a density matrix $D^{RO}$ by the regional atomic orbital basis by a Jacobi method, $C_{AO}^{RLMO}$ is a matrix representing the regional localized molecular orbital by the atomic orbital basis, and $C_{AO}^{CMO}$ is a matrix representing the canonical molecular orbital by the atomic orbital basis, so that a frozen AO region, which is localized in such a manner that the phase of the orbital is increased on one end of the starting cluster, and an active AO region, which is localized in such a manner that the phase of the orbital is increased on the other end of the starting cluster, are created; and
- instructions that cause a processor to perform a fragment-added molecular orbital computing step of computing a molecular orbit of the starting cluster added with predetermined fragments by the elongation method by solving a Fock matrix based on the regional localized molecular orbit by a self-consistent field method, and replacing the starting cluster with the starting cluster added with the predetermined fragments as a new starting cluster in a case where the starting cluster added with the predetermined fragments is not a targeted polymer, and outputting the computed molecular orbit as the computation result to the output section in a case where the starting cluster added with the predetermined fragments is a targeted polymer.

* * * * *